US007374945B2

(12) United States Patent
Becker

(10) Patent No.: US 7,374,945 B2
(45) Date of Patent: May 20, 2008

(54) METHOD FOR ENHANCING THE ASSOCIATION RATES OF POLYNUCLEOTIDES

(75) Inventor: Michael M. Becker, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 10/020,596

(22) Filed: Dec. 7, 2001

(65) Prior Publication Data

US 2002/0164614 A1 Nov. 7, 2002

Related U.S. Application Data

(60) Provisional application No. 60/255,535, filed on Dec. 14, 2000.

(51) Int. Cl.
G01N 33/00 (2006.01)
C12Q 1/68 (2006.01)
C12M 1/36 (2006.01)
C07H 21/04 (2006.01)

(52) U.S. Cl. .................. 436/94; 435/6; 435/287.2; 536/23.1; 536/24.3

(58) Field of Classification Search .............. 435/6, 435/91.1, 91.2, 183, 287.2; 536/23.5, 24.31, 536/24.3, 23.1, 24.33; 935/1, 8, 77, 78, 6; 436/518, 94, 800
See application file for complete search history.

(56) References Cited

U.S. PATENT DOCUMENTS

| | | | | |
|---|---|---|---|---|
| 4,683,202 | A | * | 7/1987 | Mullis .................. 435/91.2 |
| 4,834,854 | A | | 5/1989 | Sugihara et al. |
| 4,876,335 | A | * | 10/1989 | Yamane et al. ............ 536/24.3 |
| 5,132,207 | A | | 7/1992 | Kohne et al. |
| 5,200,314 | A | | 4/1993 | Urdea |
| 5,512,436 | A | | 4/1996 | Stone |
| 5,589,335 | A | | 12/1996 | Kearney et al. |
| 5,731,148 | A | * | 3/1998 | Becker et al. .............. 435/6 |
| 5,747,254 | A | | 5/1998 | Pontius |
| 5,753,437 | A | * | 5/1998 | Stegg .................... 435/6 |
| 5,928,869 | A | * | 7/1999 | Nadeau et al. ............. 435/6 |
| 6,017,700 | A | | 1/2000 | Horn et al. |
| 6,030,954 | A | | 2/2000 | Wu et al. |
| 6,153,596 | A | | 11/2000 | Liotta et al. |
| 6,255,476 | B1 | * | 7/2001 | Vinayak et al. ........... 536/25.32 |
| 6,281,005 | B1 | | 8/2001 | Casal et al. |
| 6,287,774 | B1 | | 9/2001 | Nikiforov |
| 6,297,016 | B1 | * | 10/2001 | Egholm .................. 435/6 |
| 6,380,377 | B1 | * | 4/2002 | Dattagupta ............... 536/24.3 |
| 6,448,407 | B1 | * | 9/2002 | Lee ..................... 546/283.1 |
| 6,465,175 | B2 | * | 10/2002 | Horn .................... 435/6 |

FOREIGN PATENT DOCUMENTS

| | | | |
|---|---|---|---|
| EP | 0610212 | B1 | 8/1994 |
| EP | 0853129 | A2 | 7/1998 |
| JP | 64-49951 | A | 2/1989 |
| WO | WO 91/08480 | * | 6/1991 |
| WO | WO 9108480 | A1 | 6/1991 |
| WO | WO 91/08480 A1 | * | 9/1991 |
| WO | WO 95/06056 | A1 | 3/1995 |
| WO | WO 97/43450 | A1 | 11/1997 |
| WO | WO0743450 A1 | * | 11/1997 |
| WO | WO 00/72016 | A1 | 11/2000 |
| WO | WO 0106011 | A2 | 1/2001 |
| WO | WO 03018841 | A | 6/2003 |

OTHER PUBLICATIONS

Majlessi et al., "Advantages of 2'-O-methyl oligoribonucleotide probes for detecting RNA targets", Nucleic Acids Research, 1998, 26(9):2224-2229.
Maruyama et al., "Characterization of Interpolyelectrolyte Complexes between Double-Stranded DNA and Polylysine Comb-Type Copolymers Having Hydrophilic Side Chains", Bioconjugate Chem., 1998, 9:292-299.
Tyagi et al., "Molecular Beacons: Probes that Fluoresce upon Hybridization", Nature Biotechnology, 1996, 14:303-308.
Asayama et al., "Design of Comb-Type Polyamine Copolymers for a Novel pH-Sensitive DNA Carrier", Bioconjug Chem, Nov.-Dec. 1997;8(6):833-8, American Chemical Society, US.
Bloomfield, "Condensation of DNA by Multivalent Cations: Considerations on Mechanism", Biopolymers, Nov. 1991;31(13):1471-81, John Wiley & Sons Incorporated, US.
Bloomfield, "DNA condensation", Curr Opin Struct Biol, Jun. 1996;6(3):334-41, Current Biology Ltd., GB.
Ferdous et al., "Comb-Type Copolymer: Stabilization of Triplex DNA and Possible Application in Antigene Strategy", J Pharm Sci, Nov. 1998;87(11):1400-5, American Pharmaceutical Association, US.
Ferdous et al., "Inhibition of Sequence-Specific Protein-DNA Interaction and Restriction Endonuclease Cleavage via Triplex Stabilization by Poly(L-lysine)-graft-dextran Copolymer", Biomacromolecules, 2000 Summer;1(2):186-93, American Chemical Society, US.
Ferdous et al., "Mechanism of Intermolecular Purine-Purine-Pyrimidine Triple Helix Stabilization by Comb-Type Polylysine Graft Copolymer at Physiologic Potassium Concentration", Bioconjug Chem, Jul.-Aug. 2000;11(4):520-6, American Chemical Society, US.
Ferdous et al., "Poly(L-lysine-graft-dextran copolymer: amazing effects on triplex stabilization under physiological pH and ionic conditions (in vitro)", Nucleic Acids Res, Sep. 1, 1998;26(17):3949-54, Oxford University Press, GB.

(Continued)

*Primary Examiner*—Bradley L. Sisson
(74) *Attorney, Agent, or Firm*—Charles B. Cappellari

(57) ABSTRACT

The present invention features a method and associated kit for increasing the association rate between polynucleotides having complementary, single-stranded regions, where the method includes providing to a test sample containing the complementary polynucleotides one or more synthetic, water soluble polycationic polymers.

9 Claims, 4 Drawing Sheets

OTHER PUBLICATIONS

Ferdous et al., "Poly(L-lysine)-graft-dextran copolymer is a novel stabilizer of triplex DNA(II): potassium-insensitive triplex formation", Nucleic Acids Symp Ser, 1997;37:301-2, Oxford University Press, GB.

Ferdous et al., "Relative Effects of Graft Copolymer and Polyamines on Triplex Stabilization Under Physiological Conditions", Nucleosides Nucleotides, Jun.-Jul. 1999;18(6-7):1651-3, Marcel Dekker Incorporated, US.

Kim et al., "Acceleration of DNA strand exchange by polycation comb-type copolymer", Nucleic Acids Symp Ser, 1999;42:139-40, Oxford University Press, GB.

Kim et al., "Comb-Type Cationic Copolymer Expedites DNA Strand Exchange while Stabilizing DNA Duplex", Chem Eur J, Jan. 5, 2001;7(1):176-80, Wiley-VCH Verlag GmbH, DE.

Luo et al., "Synthetic DNA delivery systems", Nat Biotechnol, Jan. 2000;18(1):33-7, Nature America Incorporated, US.

Majlessi et al., "Advantages of 2'-O-methyl oligoribonucleotide probes for detecting RNA targets", Nucleic Acids Res, May 1, 1998;26(9):2224-9, Oxford University Press, GB.

Maruyama et al., "Characterization of Interpolyelectrolyte Complexes between Double-Stranded DNA and Polylysine Comb-Type Copolymers Having Hydrophilic Side Chains", Bioconjug Chem, Mar.-Apr. 1998;9(2):292-9, American Chemical Society, US.

Maruyama et al., "Comb-Type Copolymers for Controlled DNA Delivery", Nucleosides Nucleotides, Jun.-Jul. 1999;18(6-7):1681-2, Marcel Dekker Incorporated, US.

Maruyama et al., "Comb-Type Polycations Effectively Stabilize DNA Triplex", Bioconjug Chem, Jan.-Feb. 1997;8(1):3-6, American Chemical Society, US.

Maruyama et al., "Nanoparticle DNA Carrier with Poly(L-lysine) Grafted Polysaccharide Copolymer and Poly(D,L-lactic acid)", Bioconjug Chem, Sep.-Oct. 1997;8(5):735-42, American Chemical Society, US.

Maruyama et al., "Poly(L-lysine)-graft-dextran copolymer is a novel stabilizer of triplex DNA (I): stabilization of poly(dA).2poly(dT) triplex", Nucleic Acids Symp Ser, 1997;37:225-6, Oxford University Press, GB.

Maruyama et al., "Preparation and evaluation of ODN conjugates with polycation comb-type copolymer", Nucleic Acids Symp Ser, 1999;42:97-8, Oxford University Press, GB.

Porschke, "Nature of Protamine-DNA Complexes A Special Type of Ligand Binding Co-operativity", J Mol Biol, Nov. 20, 1991;222(2):423-33, Academic Press Limited, GB.

Renz et al., "A colorimetric method for DNA hybridization", Nucleic Acids Res, Apr. 25, 1984; 12(8):3435-44, Oxford University Press, GB.

Sikorav, "Complementary Recognition in Condensed DNA: Accelerated DNA Renaturation", J Mol Biol, Dec. 20, 1991;222(4):1085-108, Academic Press Limited, GB.

Torigoe et al., "Poly(L-lysine)-graft-dextran Copolymer Promotes Pyrimidine Motif Triplex DNA Formation at Physiological pH", J Biol Chem, Mar. 5, 1999;274(10):6161-7, American Society for Biochemistry and Molecular Biology, US.

Torigoe et al., "Promotion mechanism of triplex DNA formation by comb-type polycations: Thermodynamic analyses of sequence specificity and ionic strength dependence", Nucleic Acids Symp Ser, 1999;42:137-8, Oxford University Press, GB.

Trubetskoy et al., "Layer-by-layer deposition of oppositely charged polyelectrolytes on the surface of condensed DNA particles", Nucleic Acids Res, Aug. 1, 1999;27(15):3090-5, Oxford University Press, GB.

Wahl et al., "Efficient transfer of large DNA fragments from agarose gels to diazobenzyloxymethyl-paper and rapid hybridization by using dextran sulfate", Proc Natl Acad Sci USA, Aug. 1979;76(8):3683-7, National Academy Press, US.

Wetmur et al., "Kinetics of Renaturation of DNA" J Mol Biol, Feb. 14, 1968;31(3):349-70, Academic Press Limited, GB.

EPO Office Action, European Patent Application No. 01 991 158.5, Dec. 14, 2007.

USPTO Office Action, U.S. Appl. No. 10/712,525, filed Mar. 11, 2005.

USPTO Final Office Action, U.S. Appl. No. 10/712,525, filed Sep. 16, 2005.

PCT Search Report, International Application No. PCT/US01/48592, Aug. 12, 2003.

PCT International Preliminary Examination Report, International Application No. PCT/US01/48592, May 12, 2005.

IPA Examination Report, Australian Patent Application No. 2002230901, May 30, 2006.

IPA Notice of Acceptance, Australian Patent Application No. 2002230901, Aug. 29, 2006.

EPO Office Action, European Patent Application No. 01 991 158.5, Feb. 20, 2007.

JPO Office Action, Japanese Patent Application No. 2002-550118, Sep. 10, 2007.

Nikiforov et al., "Detection of Hybrid Formation between Peptide Nucleic Acids and DNA by Fluorescence Polarization in the Presence of Polylysine," Anal. Biochem., 1999, 275:248-253, Academic Press, New York, USA.

* cited by examiner

METHOD FOR ENHANCING THE ASSOCIATION RATES OF POLYNUCLEOTIDES

This application claims the benefit of U.S. Provisional Application No. 60/255,535, filed Dec. 14, 2000, the contents of which are hereby incorporated by reference herein.

FIELD OF THE INVENTION

The present invention relates to a method and kit for use in forming duplexes from single-stranded, complementary regions of polynucleotides which include one or more synthetic, water soluble polycationic polymers which enhance the association rates of the polynucleotides under assay conditions.

BACKGROUND OF THE INVENTION

Nucleic acid association concerns techniques by which complementary base regions of two separate strands of nucleic acid, or distinct base regions of the same nucleic acid strand, anneal to each other through Watson-Crick base pairing, thus forming at least partially double-stranded nucleic acids. Examples of such pairing include two complementary DNA sequences, a single-stranded DNA sequence and a complementary RNA sequence, and two complementary RNA sequences, as well as modified forms of these nucleic acids, such as peptide nucleic acids or locked nucleic acids. See Nielsen et al, "Peptide Nucleic Acids," U.S. Pat. No. 5,773,571; see also Imanishi et al., "Bicyclonucleoside and Oligonucleotide Analogues," U.S. Pat. No. 6,268,490. For base pairing to take place, it is necessary to incubate the single-stranded nucleic acids under conditions which facilitate the formation of stable duplexes between nucleic acids or within a nucleic acid having complementary base regions. The formation of duplexes under stringent assay conditions can provide useful information about at least one member of each duplex, including the source from which that particular member was derived (e.g., a specific virus, microorganism, plant or animal), whether directly or by nucleic acid amplification, the presence of a disease-associated gene, the level of gene expression, the identification of genetic variability, including the detection of mutations and polymorphisms, and nucleic acid sequence information.

The rate at which nucleic acids having complementary base regions associate to form duplexes follows second-order kinetics. Thus, as the concentration of single-stranded nucleic acids is increased, the reaction rate (i.e., the rate at which duplexes are formed) is also increased. Conversely, as the concentration of single-stranded nucleic acids is decreased, the reaction rate is likewise decreased and, as a result, more time is required for the formation of double-stranded nucleic acids.

It is also well known that the temperature a reaction mixture affects the rate at which complementary nucleic acids associate. For example, as the temperature of a reaction mixture falls below the melting temperature or $T_m$ (the temperature at which 50% of the duplexed molecules are rendered single-stranded), a maximum rate of reaction will be reached at temperatures approximately 15° to 30° C. below the $T_m$. Decreasing the temperature still further will lower the reaction rate below this maximum rate.

The reaction rate between nucleic acids having complementary base regions is also very dependent upon the ionic strength of a reaction mixture. Deoxynucleic acids, for instance, show a marked increase in reaction rates up to about 1.2 M NaCl, at which point the rate of association becomes essentially constant. See Wetmur et al. *J. Mol. Biol.* (1968) 31:349-379. And hybridizations between DNA and RNA molecules show a 5-6 fold increase in the rate of association when the ionic strength is increased from 0.2 to 1.5 M NaCl. The effect of changes in salt concentration on the rate of DNA:DNA reactions is greater than it is for RNA:DNA reactions.

A major limitation on the utility of many known nucleic acid association techniques is the basic rate of the reaction. Reaction times can be on the order of several hours to tens of hours, and even days in certain instances. Increasing the reaction rate by increasing the amount of single-stranded nucleic acid molecules in a reaction, in order to take advantage of second-order kinetics, is an undesirable solution for several reasons. First, in many applications the targeted nucleic acid in a reaction mixture has been extracted from a physiological sample, thereby imposing inherent limits on the amount of the targeted nucleic acid available in the reaction mixture, at least in the absence of an amplification procedure such as the polymerase chain reaction. See, e.g., Mullis, "Process for Amplifying Nucleic Acid Sequences," U.S. Pat. No. 4,683,202. Second, there are considerable expenses associated with the use of nucleic acid reactants, and even greater expenses associated with a nucleic acid amplification procedure (e.g., enzymes and amplification primers), thus affecting the practicality of using more of these reactants or adding amplification reactants. Third, increasing the quantity of labeled, single-stranded nucleic acid probe molecules in a reaction mixture will cause a decrease in the sensitivity of a reaction, since the additional single-stranded nucleic acid probe molecules will elevate the background noise.

Accordingly, it is a principal object of the present invention to provide a method for forming a duplex from single-stranded regions of separate polynucleotides which enhances the association rate of the polynucleotides, whether reassociation or hybridization, and which enhancement can be demonstrated using reference conditions, including those conditions set forth herein. It is a further object of the present invention to provide a method for enhancing association rates that would be applicable to DNA:DNA, RNA:DNA and RNA:RNA reaction systems. Additionally, it is an object of the present invention to provide a method for promoting polynucleotide association rates that is applicable to reaction mixtures having a range of temperature and ionic strength conditions.

SUMMARY OF THE INVENTION

In satisfaction of these objectives, the present invention features a method for forming a duplex from a polynucleotide probe and a target nucleic acid, where the method comprises the steps of: (i) providing the probe to a test sample under conditions permitting the probe to preferentially hybridize to the target nucleic acid, if any, present in the sample; and (ii) providing a synthetic polycationic polymer to the test sample in an amount sufficient to increase the association rate of the probe and the target nucleic acid in the sample under the conditions permitting the probe to preferentially hybridize to the target nucleic acid. To facilitate detecting the formation of probe:target nucleic acid hybrids, this method may further comprise providing to the test sample a reagent to dissociate the polymer from the probe in some detection systems. Additionally, this method may be used in an assay to determine the presence or absence of a target nucleic acid sequence derived from a target virus or organism or a target group of viruses or organisms as an indication of the presence or absence of the target virus or organism or members of the target group of viruses or organisms in the test sample. Alternative uses of this method include detecting the presence of a disease-associated gene, determining the state of a disease, measuring levels of gene expression, and detecting mutations or polymorphisms in a test sample.

In addition to anionic groups, polynucleotide probes featured in the present invention may further include cationic and/or nonionic groups, provided the probes have a net negative charge. The polynucleotide may consist of deoxyribonucleic acid (DNA), ribonucleic acid (RNA), a combination of DNA and RNA, or it may include a nucleic acid analog (e.g., a peptide nucleic acid) or contain one or more modified nucleosides (e.g., a ribonucleoside having a 2'-O-methyl substitution to the ribofuranosyl moiety). Non-nucleotide groups, such as polysaccharides or polyethyelene glycol, may also be included in the probes, provided they do not prevent or substantially interfere with hybridization of the probe to the target nucleic acid. Probes of the present invention are up to 100 bases or more in length (preferably from 12 to 50 bases, and more preferably from 18 to 35 bases in length) and contain a base region which is complementary to a target sequence contained in the target nucleic acid (the base region is preferably perfectly complementary to the target sequence).

The probes preferably include a detectable label or group of interacting labels. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably bind to the target nucleic acid under the stated conditions, and mixtures of these. In one particularly preferred embodiment, the label is an acridinium ester (AE), preferably 4-(2-succinimidyloxycarbonyl ethyl)-phenyl-10-methylacridinium-9-carboxylate fluorosulfonate (hereinafter referred to as "standard AE"). Groups of interacting labels include, but are not limited to, enzyme/substrate, enzyme/cofactor, luminescent/quencher, luminescent/adduct, dye dimers and Förrester energy transfer pairs. When provided with a group of interacting labels, the probes preferably have regions of self-complementarity such that the group of interacting labels produce a first signal when an associated probe is self-hybridized and a second signal when the probe is hybridized to the target nucleic acid, where the first and second signals are differentially detectable. In some embodiments, these regions of self-complementarity may overlap or include the portion or portions of the probe which hybridize to the target nucleic acid.

To isolate the target nucleic acid in a test sample prior to detection, the present invention further contemplates probes having a base sequence region distinct from the target binding region of the probe which constitutes an immobilized probe binding region of a capture probe. The immobilized probe binding region may be comprised of, for example, a 3' poly dA (adenine) region which hybridizes under stringent conditions to a 5' poly dT (thymine) region of a polynucleotide bound directly or indirectly to a solid support provided to the test sample. Any known solid support may be used, such as matrices and particles free in solution. The solid support may be, for example, nitrocellulose, nylon, glass, polyacrylate, mixed polymers, polystyrene, silane polypropylene and, preferably, particles having a magnetic charge to facilitate recovering sample and/or removing unbound nucleic acids or other sample components. Particularly preferred supports are magnetic spheres that are monodisperse (i.e., uniform in size ±5%), allowing for consistent results, which is particularly advantageous for use in an automated procedure.

The target nucleic acid may be RNA or DNA, a nucleic acid analog or a chimeric containing different types of nucleic acid and/or nucleic acid analogs. A preferred target nucleic acid of the present invention is RNA, especially ribosomal RNA (rRNA) and messenger RNA (mRNA). Ribosomal RNA is a preferred target nucleic acid for detecting groups of organisms in test samples because of its relative abundance in cells and because of its conserved nature which allows for differentiating between defined groups of organisms. See, e.g., Kohne, "Method for Detecting, Identifying, and Quantitating Organisms and Viruses," U.S. Pat. No. 5,288,611, and Hogan et al., "Nucleic Acid Probes for Detection and/or Quantitation of Non-Viral Organisms," U.S. Pat. No. 5,840,488. For measuring gene expression, determining the presence of a particular cell-type, or detecting the presence of a target group of viruses, assaying for specific mRNAs may be preferred. See, e.g., Gentalen et al., "Methods of Using an Array of Pooled Probes in Genetic Analysis," U.S. Pat. No. 6,306,643; Kohne, "Method for Detecting the Presence of RNA Belonging to an Organ or Tissue Cell-Type," U.S. Pat. No. 5,932,416; and Kohne, "Method for Detecting the Presence of Group-Specific Viral mRNA in a Sample," U.S. Pat. No. 5,955,261.

The sensitivity of an assay is limited by the amount of target nucleic acid present in the test sample. To increase the sensitivity of a detection assay, the present invention further contemplates an amplification step to increase the quantity of the target nucleic acid in the test sample prior to detection with a polynucleotide probe. Thus, the target nucleic acid may be directly obtained from the test sample or it may be a nucleic acid derived from an amplification procedure (i.e., amplicon). Numerous amplification procedures are well known in the art, the most common of which is the polymerase chain reaction. See, e.g., Mullis in U.S. Pat. No. 4,683,202. Amplification may be performed in the presence of non-target nucleic acid or the target nucleic acid may be isolated and purified prior to amplification in order to remove inhibitors of amplification and to limit non-specific amplification.

The polycationic polymers and polynucleotide probes of the present invention may be provided to the test sample in any order. The polymers are synthetically produced and water soluble. They include a plurality of cationic charges and may be homopolymers and/or copolymers, including block and graft copolymers. While the polymers may include ionic and/or anionic monomers, the positively charged monomers are present in molar excess to the negatively charged monomers. The cationic charges of the polymers may be localized or delocalized or they may include both localized and delocalized cationic charges.

In a preferred embodiment, the polycationic polymers of the present invention form complexes of nanoparticle size in the test sample under hybridization assay conditions. These complexes may include a plurality of covalently linked polymers, and may further include covalently linked polymers and polynucleotides. To prevent their precipitation out of solution, these complexes are preferably water soluble. Thus, the cationic monomers present in the polymers are preferably present in molar excess of the phosphate groups of the probes provided to a test sample, and even more preferably present in molar excess of the phosphate groups of all nucleic acids predicted to be present in a test sample.

In certain embodiments of the present invention, it is desirable to dissociate polymers and polynucleotides prior to detection of the target nucleic acid, if present, and after complementary polynucleotides have had sufficient time to stably associate in the test sample. Dissociation can be achieved by providing one or more dissociating agents to the test sample, such as an anionic detergent (e.g., lithium lauryl sulfate) and/or a polyanion (e.g., exogenous nucleic acid). The dissociating agents should be provided to the test sample in an amount sufficient to weaken the bonds between polymers and polynucleotides.

The association rate of complementary polynucleotides in the presence of the polycationic polymers of the present invention is preferably at least about 2-fold greater than the association rate of the same complementary polynucleotides in the absence of the polymer under identical incubation periods and conditions. More preferably, the association rate is at least about 5-fold greater, at least about 10-fold greater, at least about 100-fold greater or at least about 1000-fold greater in the presence of the polycationic polymers. Such conditions preferably include a temperature of at least about 40° C. and a salt concentration of at least about 5 mM monovalent cations (or an equivalent salt concentration including multivalent cations, such as divalent magnesium present in magnesium chloride or magnesium sulfate). More preferably, such conditions include a temperature of at least about 40° C. and a salt concentration of at least about 150 mM monovalent cations (or an equivalent salt concentration including multivalent cations). An equivalent salt concentration is one which will result in approximately the same rate enhancement as a salt concentration which does not include any multivalent cations under otherwise identical conditions. The temperature of the reaction mixture will generally be in the range of room temperature to about 90° C., and is preferably in the range of about 40° C. to about 70° C., more preferably in the range of about 50° C. to about 60° C., and is most preferably about 60° C.

In a further embodiment of the present invention, a kit is featured which comprises: (i) a polynucleotide probe which preferentially hybridizes to a target nucleic acid sequence in a test sample under hybridization assay conditions; and (ii) a synthetic polycationic polymer in an amount sufficient to increase the association rate of the probe and the target sequence in the test sample under the hybridization assay conditions. The probe and polymer may be provided in the same or separate containers. Kits according to the present invention may further comprise at least one of the following: (i) a reagent to dissociate the polymer from the probe; (ii) one or more amplification primers for amplifying a target sequence contained in or derived from the target nucleic acid; (iii) a capture probe for isolating and purifying target nucleic acid present in a test sample; and (iv) if a capture probe is included, a solid support material (e.g., magnetically responsive particles) for immobilizing the capture probe, either directly or indirectly, in a test sample. Where the target nucleic acid is a structured nucleic acid having regions of self-complementarity, such as rRNA, the kits of the present invention may further include helper probes. See Hogan et al., "Means and Method for Enhancing Nucleic Acid Hybridization," U.S. Pat. No. 5,030,557. Additionally, the kits may comprise written instructions for performing an assay to determine the presence or absence of a target nucleic acid sequence in the test sample as an indication of the presence or absence of a target virus or organism or members of a target group of viruses or organisms in the test sample. The assay described in the written instructions may include steps for isolating and purifying the target nucleic acid prior to detection with the polynucleotide probe and/or amplifying a target sequence contained in the target nucleic acid. Alternatively, the kit may include written instructions for performing, for example, an assay to detect the presence of a disease-associated gene, to determine the state of a disease, to measure levels of gene expression, or to detect mutations or polymorphisms in a test sample.

Other features and advantages of the invention will be apparent from the following description of the preferred embodiments thereof and from the claims.

DESCRIPTION OF THE PREFERRED EMBODIMENTS

A. Definitions

Figure 1:
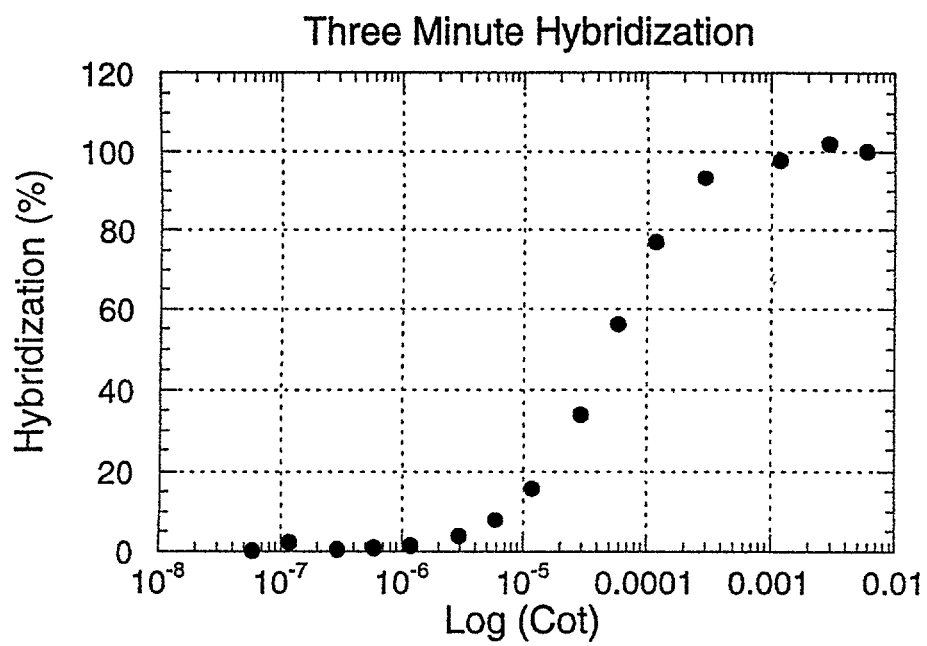
FIG. 1 is a plot of percent hybridization versus log of $C_o t$ for a range of target concentrations used to determine the rate of a reaction having a three minute incubation period, where each (●) represents a data point derived from experimental data.

The following terms have the indicated meanings in the specification unless expressly indicated to have a different meaning.

By "target nucleic acid," "target polynucleotide" or "target" is meant a nucleic acid containing a target nucleic acid sequence.

By "target nucleic acid sequence," "target sequence" or "target region" is meant a specific deoxyribonucleotide or ribonucleotide sequence comprising all or part of the nucleotide sequence of a single-stranded nucleic acid molecule. Target nucleic acid sequences of the present invention contain a mixture of nucleotides, i.e., more than one type of nucleotide (e.g., adenine (A), cytosine (T), guanine (G), inosine (I), thymine (T) or uracil (U)).

By "polynucleotide" is meant a polymer having two or more nucleoside subunits or nucleobase subunits coupled together. The polynucleotides include DNA and/or RNA or analogs thereof and may further include non-nucleotide groups such as, for example, abasic nucleotides, universal bases (e.g., 3-nitropyrrole and 5-nitroindole), polysaccharides, peptides, polypeptides and/or polyethylene glycol. See, e.g., Becker et al., "Molecular Torches," U.S. Pat. No. 6,361,945; Bergstrom et al., "3-Nitropyrrole Nucleoside," U.S. Pat. No. 5,681,947; Loakes et al. *Nucleic Acids Research* (1995) 23(13):2361-2366; and Arnold et al., "Linking Reagents for Nucleotide Probes," U.S. Pat. No. 5,585,481. The sugar groups of the nucleoside subunits may be ribose, deoxyribose and analogs thereof, including, for example, ribonucleosides having a 2'-O-methyl substitution to the ribofuranosyl moiety. (Polynucleotides including nucleoside subunits having 2' substitutions which are useful as polynucleotide probes are disclosed by Becker et al., "Method for Amplifying Target Nucleic Acid Using Modified Primers," U.S. Pat. No. 6,130,038.) The nucleoside subunits may by joined by linkages such as phosphodiester linkages, modified linkages or by non-nucleotide moieties which do not prevent hybridization of the polynucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing at least a portion of the natural deoxyribose phosphate backbone of DNA with a pseudo peptide backbone, such as a 2-aminoethylglycine backbone which couples the nucleobase subunits by means of a carboxymethyl linker to the central secondary amine. (DNA analogs having a pseudo peptide backbone are commonly referred to as "peptide nucleic acids" or "PNA" and are disclosed by Nielsen et al. in U.S. Pat. No. 5,773,571.) Other non-limiting examples of polynucleotides contemplated by the present invention include nucleic acid analogs containing bicyclic and tricyclic nucleoside and nucleotide analogs referred to as "Locked Nucleic Acids," "Locked Nucleoside Analogues" or "LNA." (Locked Nucleic Acids are disclosed by Wang, "Conformationally Locked Nucleosides and Oligonucleotides," U.S. Pat. No. 6,083,482; Imanishi et al. in U.S. Pat. No. 6,268,490; and Wengel et al., "Oligonucleotide Analogues," International Publication No. WO 99/14226.) Any nucleic acid analog is contemplated by the present invention provided the modified polynucleotide can form a stable hybrid with a target nucleic acid under hybridization assay conditions and at least a portion of the modified polynucleotide is anionic. In the case of polynucleotide probes, the modified polynucleotide must be capable of preferentially hybridizing to the target nucleic acid under hybridization assay conditions. Unless indicated to be a "probe," a polynucleotide, as used herein, may be a nucleic acid molecule obtained from a natural source which is at least partially single-stranded or which may be rendered partially or fully single-stranded by human intervention.

By "polynucleotide probe" or "probe" is meant a polynucleotide having a base sequence sufficiently complementary to its target nucleic acid sequence to form a probe:target hybrid stable for detection under hybridization assay conditions. As would be understood by someone having ordinary skill in the art, a probe is an isolated nucleic acid molecule, or an analog thereof, in a form not found in nature without human intervention (e.g., recombined with foreign nucleic acid, isolated, or purified to some extent). Probes may have additional nucleosides or nucleobases outside of the targeted region so long as such nucleosides or nucleobases do not prevent hybridization under hybridization assay conditions and, where indicated, do not prevent preferential hybridization to the target nucleic acid. A non-complementary sequence may also be included, such as a target capture sequence (generally a homopolymer tract, such as a poly-A, poly-T or poly-U tail) or sequences which will confer a desired secondary or tertiary structure, such as a hairpin structure, which can be used to facilitate detection. Examples of probes having a target capture sequence ("capture probes") are disclosed by Ranki et al., "Detection of Microbial Nucleic Acids by a One-Step Sandwich Hybridization Test," U.S. Pat. No. 4,486,539; Stabinsky, "Methods and Kits for Performing Nucleic Acid Hybridization Assays," U.S. Pat. No. 4,751,177; and Weisburg et al., "Two Step Hybridization and Capture of a Polynucleotide," U.S. Pat. No. 6,110,678. Self-hybridizing probes are disclosed by, for example, Bagwell, "Fluorescent Imperfect Nucleic Acid Probes," U.S. Pat. No. 5,607,834; Tyagi et al., "Detectably Labeled Dual Conformation Oligonucleotide Probes, Assays and Kits," U.S. Pat. No. 5,925,517; and Becker et al. in U.S. Pat. No. 6,361,945.

Polynucleotide probes of the present invention are preferably no more than about 100 bases in length, more preferably no more than about 50 bases in length, and most preferably no more than about 35 bases in length. Probes of a defined sequence may be produced by techniques known to those of ordinary skill in the art, such as by chemical or biochemical synthesis, and by in vitro or in vivo expression from recombinant nucleic acid molecules, e.g., bacterial or retroviral vectors.

By "complementary" is meant polynucleotides having base sequence regions able to form stable hydrogen bonds under hybridization assay conditions. Perfect complementarity between base regions of polynucleotides is not required, provided the two regions are sufficiently complementary to permit the stable formation of a double-stranded, hydrogen-bonded region under hybridization assay conditions.

By "stably," "stable" or "stable for detection" is meant that the temperature of a reaction mixture is at least 2° C. below the melting temperature of a polynucleotide duplex. The temperature of the reaction mixture is more preferably at least 5° C. below the melting temperature of the polynucleotide duplex, and even more preferably at least 10° C. below the melting temperature of the reaction mixture.

By "hybridization" is meant the ability of two completely or partially complementary polynucleotides to come together under specified hybridization assay conditions in an orientation permitting the formation of a stable structure having a double-stranded region. The two constituent strands of this double-stranded structure, sometimes called a hybrid, are held together by hydrogen bonds. Although these hydrogen bonds most commonly form between the bases of adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., ROGER L. P. ADAMS ET AL., THE BIOCHEMISTRY OF THE NUCLEIC ACIDS (11$^{th}$ ed. 1992).)

By "preferentially hybridize" is meant that under the specified hybridization assay conditions, polynucleotide probes can hybridize to their target nucleic acids to form stable probe:target hybrids indicating the presence of a specific target nucleic acid sequence, and there is not formed a sufficient number of stable probe:non-target hybrids to indicate the presence of non-target nucleic acids. Thus, the probe hybridizes to target nucleic acid to a sufficiently greater extent than to non-target nucleic acid to enable one having ordinary skill in the art to accurately detect the presence (or absence) of the target nucleic acid sequence in a test sample which may also contain non-target nucleic acid. Probes which preferentially hybridize to target nucleic acid are particularly useful in diagnostic assays intended to specifically detect the presence or absence of a particular virus or organism or members of a group of viruses or organisms in a test sample which may also contain phylogenetically closely related non-target viruses or organisms. Such diagnostic assays are well known in the art and are disclosed by, for example, Kohne in U.S. Pat. No. 5,288,611.

In general, reducing the degree of complementarity between a polynucleotide sequence and its target sequence will decrease the degree or rate of hybridization of the polynucleotide to its target region. However, the inclusion of one or more non-complementary bases may facilitate the ability of a polynucleotide to discriminate against non-target polynucleotides.

Preferential hybridization can be measured using techniques well known to those having ordinary skill in the art, including those described in the Examples section infra. Preferably, there is at least a 10-fold difference between target and non-target hybridization signals in a test sample, more preferably at least a 100-fold difference, and most preferably at least a 1,000-fold difference. Preferably, non-target hybridization signals in a test sample are no more than the background signal level.

By "phylogenetically closely related" is meant that the organisms or viruses are closely related to each other in an evolutionary sense and therefore would have a higher total nucleic acid sequence homology than organisms or viruses that are more distantly related. Organisms or viruses occupying adjacent and next to adjacent positions on the phylogenetic tree are closely related. Organisms or viruses occupying positions farther away than adjacent or next to adjacent positions on the phylogenetic tree will still be closely related if they have significant total nucleic acid sequence homology.

By "test sample" is meant a substance known or suspected to contain target nucleic acid extracted or removed from any source, including bodily fluids, tissues, secretions and excretions, plants, water, food and the environment, for assaying in vitro or ex vivo. The substance may be processed to isolate and purify nucleic acid contained therein, such that use of the term "test sample" herein may refer to either the substance in its unaltered, extracted state or to target nucleic acid which has been isolated from the substance and then purified.

By "capture probe" is meant a polynucleotide or a set of at least two polynucleotides linked together which are capable of hybridizing to a target nucleic acid and to an immobilized probe, thereby providing means for immobilizing and isolating the target nucleic acid in a test sample. That portion of the capture probe which hybridizes to the target nucleic acid is referred to as the "target binding region," and that portion of the capture probe which hybridizes to the immobilized probe is referred to as the "immobilized probe binding region." While the capture probe hybridizes to both the target nucleic acid and the immobilized probe under hybridization assay conditions, the target binding region and the immobilized probe binding region may be designed to hybridize to their respective target sequences under different hybridization assay conditions. In this way, the capture probe may be designed so that it first hybridizes to the target nucleic acid under more favorable in solution kinetics before adjusting the conditions to permit hybridization of the immobilized probe binding region to the immobilized probe. The target binding and immobilized probe binding regions may be directly adjoining each other on the same polynucleotide, they may be separated from each other by one or more optionally modified nucleotides, and/or they may be joined to each other by means of a non-nucleotide linker.

By "target binding region" is meant that portion of a polynucleotide which stably binds to a target sequence present in a target nucleic acid, a DNA or RNA equivalent of the target sequence or a complement of the target sequence under hybridization assay conditions. The hybridization assay conditions may be stringent hybridization assay conditions or amplification conditions.

By "immobilized probe binding region" is meant that portion of a polynucleotide which hybridizes to an immobilized probe under hybridization assay conditions.

By "immobilized probe" is meant a polynucleotide for joining a capture probe to an immobilized support. The immobilized probe is joined either directly or indirectly to the solid support by a linkage or interaction which remains stable under the conditions employed to hybridize the capture probe to the target nucleic acid and to the immobilized probe, whether those conditions are the same or different. The immobilized probe facilitates separation of the bound target nucleic acid from unbound materials in a sample.

By "isolate," "isolated" or "isolating" is meant that at least a portion of the target nucleic acid present in a test sample is concentrated in a reaction receptacle or on a reaction device or solid carrier (e.g., test tube, cuvette, microtiter plate well, nitrocellulose filter, slide or pipette tip) in a fixed or releasable manner so that the target nucleic acid can be purified without significant loss of the target nucleic acid from the receptacle, device or carrier.

By "purify," "purified" or "purifying" is meant that one or more components of a sample present in a reaction receptacle or on a reaction device or solid carrier are physically removed from one or more other sample components present in the reaction receptacle or on the reaction device or solid carrier. Sample components which may be removed during a separating or purifying step include proteins, carbohydrates, lipids, inhibitors, non-target nucleic acids and unbound probe. Preferably retained in a sample during a purifying step are target nucleic acids bound to immobilized capture probes.

By "reaction mixture" is meant a test sample containing a polynucleotide probe having a base region which is complementary to a target sequence contained in a target nucleic acid known or suspected to be present in the test sample. The reaction mixture is subjected to conditions which facilitate hybridization of the probe to the target sequence.

By "hybridization conditions" or "hybridization assay conditions" is meant conditions permitting a polynucleotide probe to stably hybridize to a target nucleic acid. Hybridization assay conditions may vary depending upon factors including the GC (guanine/cytosine) content and length of the probe, the degree of similarity between the probe sequence and sequences of non-target nucleic acids which may be present in the test sample, and the target sequence. Hybridization assay conditions include the temperature and composition of the hybridization reagents or solutions. While the Examples section infra provides preferred hybridization assay conditions for detecting target nucleic acids, other acceptable conditions could be easily ascertained by someone having ordinary skill in the art.

By "reaction rate," "rate of reaction," "association rate" or "rate of association" is meant the rate at which polynucleotides having regions of complementarity reassociate or hybridize to form duplexes under hybridization assay conditions.

By "reassociation," "reassociate," "renaturation" or "renaturate" is meant the reformation of double-stranded polynucleotides from single-stranded polynucleotides which were base-paired to each other before being separated through a denaturation process.

By "hybridization" or "hybridize" is meant the formation of double-stranded polynucleotides from single-stranded polynucleotides of individual origin with respect to each other (e.g., DNA from different species or a mixture of RNA and DNA). As used herein, the term "hybridization" is used interchangeably to refer to hybridization or reassociation.

By "solution hybridization" or "in solution" is meant that the reactants present in a reaction mixture (i.e., polynucleotides having complementary, single-stranded regions) are diffusible in the reaction mixture when they are exposed to hybridization assay conditions.

By "label" is meant a reporter moiety associated with a polynucleotide which can be detected by means well known in the art and used to indicate the presence or absence of a particular polynucleotide sequence in a test sample. Examples of labels which are well known in the art include chemiluminescent, electrochemiluminescent and fluorescent compounds, radioisotopes, dyes, polynucleotides, enzymes, enzyme substrates, chromophores and haptens. When multiple interacting labels are associated with a polynucleotide, interacting labels may include, for example, the following: luminescent and quencher labels, luminescent and adduct labels, dye dimer labels, enzyme and substrate labels, enzyme and cofactor labels, and Förrester energy transfer pairs. Examples of polynucleotides having multiple interacting labels are disclosed by, for example, Bagwell in U.S. Pat. No. 5,607,834; Tyagi et al. in U.S. Pat. No. 5,925,517; and Becker et al. in U.S. Pat. No. 6,361,945.

By "nucleic acid duplex," "duplex," "nucleic acid hybrid" or "hybrid" is meant a stable nucleic acid structure comprising a double-stranded, hydrogen-bonded region. Such hybrids include RNA:RNA, RNA:DNA and DNA:DNA duplex molecules and analogs thereof. The structure is sufficiently stable to be detectable by any known means, including means which do not require a probe associated label. For instance, the detection method may include a probe coated substrate which is optically active and sensitive to changes in mass at its surface. Mass changes result in different reflective and transmissive properties of the optically active substrate in response to light and serve to indicate the presence or amount of immobilized target nucleic acid. This exemplary form of optical detection is disclosed by Nygren et al., "Devices and Methods for Optical Detection of Nucleic Acid Hybridization," U.S. Pat. No. 6,060,237. Other detection methods include those based on detecting probe associated changes in conductivity or turbidity in the test sample.

By "helper probe" is meant a polynucleotide designed to hybridize to a target nucleic acid at a different locus than that of a polynucleotide probe, thereby either increasing the rate of hybridization of the probe to the target nucleic acid, increasing the melting temperature of the probe:target hybrid, or both.

By "amplification primer" or "primer" is meant a polynucleotide capable of hybridizing to a target nucleic acid and acting as a primer and/or a promoter template (e.g., for synthesis of a complementary strand, thereby forming a functional promoter sequence) for the initiation of nucleic acid synthesis. If the amplification primer is designed to initiate RNA synthesis, the primer may contain a base sequence which is non-complementary to the target sequence but which is recognized by an RNA polymerase, such as a T7, T3 or SP6 RNA polymerase. An amplification primer may contain a 3' terminus which is modified to prevent or lessen the rate or amount of primer extension. (McDonough et al. disclose primers and promoter-primers having modified or blocked 3'-ends in U.S. Pat. No. 5,766,849, entitled "Methods of Amplifying Nucleic Acids Using Promoter-Containing Primer Sequences.") While the amplification primers of the present invention may be chemically synthesized or derived from a vector, they are not naturally-occurring nucleic acid molecules.

By "nucleic acid amplification," "target amplification" or "amplification" is meant increasing the number of nucleic acid molecules having at least one target nucleic acid sequence. Target amplification according to the present invention may be either linear or exponential, although exponential amplification is preferred.

By "amplicon" is meant a nucleic acid molecule generated in a nucleic acid amplification reaction and which is derived from a target nucleic acid. An amplicon contains a target nucleic acid sequence which may be of the same or opposite sense as the target nucleic acid.

By "derived" is meant that the referred to nucleic acid is obtained directly from a target organism or indirectly as the product of a nucleic acid amplification, which product may be, for instance, an antisense RNA molecule which does not exist in the target organism.

By "polymer" is meant a macromolecule comprising one or more repeated monomer types of low relative molecular mass covalently joined together.

By "polycationic polymer" is meant a polymer having a net positive charge, whether the charges of the polymer are localized or delocalized. A polycationic polymer is comprised of at least one cationic monomer type and may also include anionic and/or nonionic monomer types, provided the polymer has a net positive charge.

By "monomer" is meant a molecule which can undergo polymerization, thereby contributing constitutional units to the essential structure of a polymer.

By "constitutional units" is meant an atom or group of atoms (including pendant atoms or groups, if any) comprising a part of the essential structure of a polymer.

By "block copolymer" is meant a polymer composed of blocks in linear sequence.

By "block" is meant a portion of a polymer, comprising many constitutional units, which has at least one feature that is not present in adjacent portions of the polymer.

By "graft copolymer" is meant a polymer having one or more species of block connected to the main chain of the polymer as side chains. These side chains have constitutional or configurational features that differ from those of the main chain.

By "synthetic" is meant that the polymerization of the polymer did not occur exclusively in nature without human intervention.

By "complex" is meant a composition comprising a plurality of polycationic polymers. Complexes of the present invention are generally nanoparticles.

By "degree of polymerization" or "DP" is meant the number of repeating units in a polymer chain.

By "number-average molecular weight" or "$M_n$" is meant a value equal to the weight of a polymer mixture divided by the number of molecules in the mixture. The number-average molecular weight can be determined by various well known methods, including colligative properties, osmotic pressure and freezing point depression methods.

By "weight-average molecular weight" or "$M_w$" is meant the average molecular weight of the molecules in a polymer mixture. The weight-average molecular weight can be determined by a number of different well known methods, including light-scattering and ultracentrifuge methods. While the $M_w$ value and the $M_n$ value may be the same if all of the molecules in a mixture have essentially the same weight, the $M_w$ value will be higher than the $M_n$ value if some of the molecules in the mixture are heavier than others.

By "polydispersity" is meant the ratio of the weight-average molecular weight and number-average molecular weight ($M_w/M_n$) in a polymer mixture. The polydispersity value indicates how wide the range of molecular weights is in a mixture.

The following abbreviations have the indicated meanings: "Da"=daltons; "M"=moles/liter; "s"=seconds; and "m"=minutes.

B. Hybridization Conditions and Probe Design

Hybridization reaction conditions, most importantly the temperature of hybridization and the concentration of salt in the hybridization solution, can be selected to allow a polynucleotide probe to preferentially hybridize to a target nucleic acid and not to non-target nucleic acid known or suspected of being present in a test sample. At decreased salt concentrations and/or increased temperatures (conditions of increased stringency) the extent of hybridization decreases as hydrogen bonding between paired nucleotide bases in the double-stranded hybrid molecule is disrupted. This process is known as "melting."

Generally speaking, the most stable hybrids are those having the largest number of contiguous, perfectly matched (i.e., hydrogen-bonded) nucleotide base pairs. Such hybrids would usually be expected to be the last to melt as the stringency of the hybridization conditions increases. However, a double-stranded nucleic acid region containing one or more mismatched, "non-canonical," or imperfect base pairs (resulting in weaker or non-existent base pairing at that position in the nucleotide sequence of a nucleic acid) may still be sufficiently stable under conditions of relatively high stringency to allow the nucleic acid hybrid to be formed and detected in a hybridization assay without cross-reacting with other, non-selected nucleic acids which may be present in a test sample.

Hence, depending on the degree of similarity between the nucleotide sequences of the target nucleic acid and those of non-target nucleic acids present in the test sample on one hand, and the degree of complementarity between the base sequence of a particular probe and the nucleotide sequences of the target and non-target nucleic acids on the other, one or more mismatches will not necessarily defeat the ability of a probe to hybridize to the target nucleic acid and not to non-target nucleic acids present in the test sample.

Polynucleotide probes useful in the present invention are preferably chosen, selected, and/or designed to maximize the difference between the melting temperatures $T_m$ of the probe:target hybrid and the $T_m$ of a mismatched hybrid formed between the probe and non-target nucleic acid present in the test sample (e.g., nucleic acid, such as ribosomal RNA (rRNA), from a phylogenetically closely-related organism).

Where the target nucleic acid is rRNA, it is important to note that within the rRNA molecule there is a close relationship between secondary structure (caused in part by intra-molecular hydrogen bonding) and function. This fact imposes restrictions on evolutionary changes in the primary nucleotide sequence causing the secondary structure to be maintained. For example, if a base is changed in one "strand" of a double helix (due to intra-molecular hydrogen bonding, both "strands" are part of the same rRNA molecule), a compensating substitution usually occurs in the primary sequence of the other "strand" in order to preserve complementarity (this is referred to as co-variance), and thus the necessary secondary structure. This allows two very different rRNA sequences to be aligned based both on the conserved primary sequence and also on the conserved secondary structure elements. Potential target sequences for the polynucleotide probes can be identified by noting variations in the homology of the aligned sequences.

Merely identifying a putatively unique potential target nucleotide sequence does not guarantee that a functionally specific polynucleotide probe may be made to hybridize to nucleic acid comprising that sequence. Various other factors will determine the suitability of a nucleic acid locus as a target site for a specific probe. Because the extent and specificity of hybridization reactions, such as those described herein, are affected by a number of factors, manipulation of one or more of those factors will determine the exact sensitivity and specificity of a particular polynucleotide, whether perfectly complementary to its target or not. The importance and effect of various hybridization assay conditions are known to those skilled in the art and are disclosed by, for example, Kohne, "Method for Detection, Identification and Quantitation of Non-Viral Organisms," U.S. Pat. No. 4,851,330; Hogan et al., "Nucleic Acid Probes to *Mycobacterium gordonae*," U.S. Pat. No. 5,216,143; and Hogan, "Nucleic Acid Probes for Detection and/or Quantitation of Non-Viral Organisms," U.S. Pat. No. 5,840,488.

The desired temperature of hybridization and the hybridization solution composition (such as salt concentration, detergents and other solutes) can also greatly affect the stability of double-stranded hybrids. Conditions such as ionic strength and the temperature at which a probe will be allowed to hybridize to a target must be taken into account in constructing a probe. As noted above, the thermal stability of hybrid polynuceotides generally increases with the ionic strength of the reaction mixture. On the other hand, chemical reagents which disrupt hydrogen bonds, such as formamide, urea, dimethyl sulfoxide and alcohols, can greatly reduce the thermal stability of the hybrids.

To maximize the specificity of a probe for its target, probes should be designed to hybridize to their targets under conditions of high stringency. Under such conditions only polynucleotides (or regions) having a high degree of complementarity will hybridize to each other. Polynucleotides without such a high degree of complementarity will not form hybrids. Accordingly, the stringency of the hybridization assay conditions determines the amount of complementarity which should exist between two polynucleotides in order to form a hybrid. Stringency is chosen to maximize the difference in stability between the hybrid formed between the probe and the target nucleic acid and potential hybrids between the probe and any non-target nucleic acids present in a test sample.

While probes having extensive self-complementarity are generally avoided, there are some applications in which probes exhibiting at least some degree of self-complementarity are desirable to facilitate detection of probe:target duplexes in the presence of unhybridized probe. By way of example, structures referred to as "Molecular Torches" are designed to include distinct regions of self-complementarity (coined the "target binding domain" and the "target closing domain") which are connected by a polynucleotide and/or non-nucleotide joining region and hybridize to one another under predetermined hybridization assay conditions. When exposed to denaturing conditions, the two complementary regions (which may be fully or partially complementary) of the Molecular Torch melt, leaving the target binding domain available for hybridization to a target sequence when the predetermined hybridization assay conditions are restored. Molecular Torches are designed so that the target binding domain favors hybridization to the target sequence over the target closing domain. The target binding domain and the target closing domain of a Molecular Torch include interacting labels (e.g., luminescent/quencher) positioned so that a different signal is produced when the Molecular Torch is self-hybridized than when the Molecular Torch is hybridized to a target nucleic acid, thereby permitting detection of probe:target duplexes in a test sample in the presence of unhybridized probe having viable labels associated therewith. (Molecular Torches are disclosed by Becker et al. in U.S. Pat. No. 6,361,945.) In accordance with the teachings of Becker, probes of the present invention may be designed and constructed to include, in addition to a "target binding domain" able to distinguish target nucleic acid from non-target nucleic acid, a "target closing domain," a "joining region" and interacting labels characteristic of a Molecular Torch.

Another example of a self-complementary probe is a structure known as a "Molecular Beacon." Molecular Beacons include nucleic acid molecules having a target complement sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complement sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). (Molecular Beacons are disclosed by Tyagi et al. in U.S. Pat. No. 5,925,517.) In accordance with the teachings of Tyagi, probes of the present invention may be designed and constructed to include, in addition to a "target complement sequence" able to distinguish target nucleic acid from non-target nucleic acid, an "affinity pair" and dual labels characteristic of a Molecular Beacon.

Specificity may be achieved by limiting that portion of the polynucleotide probe having perfect complementarity to non-target sequences, by avoiding G and C rich regions of complementarity to non-target nucleic acids, and by constructing the probe to contain as many destabilizing mismatches to non-target sequences as possible. Whether a probe is appropriate for detecting a specific target nucleic acid depends largely on the thermal stability difference between probe:target hybrids versus probe:non-target hybrids. In designing probes, the differences in these $T_m$ values should be as large as possible (preferably 2° to 5° C. or more). Manipulation of the $T_m$ can be accomplished by changes to probe length and probe composition, such as GC content versus AT content or the inclusion of nucleotide analogs (e.g., ribonucleotides having a 2'-O-methyl substitution to the ribofuranosyl moiety).

In general, the optimal hybridization temperature for polynucleotide probes is approximately 5° C. below the melting temperature for a given duplex. Incubation at temperatures below the optimum temperature may allow mismatched base sequences to hybridize and can therefore decrease specificity. The longer the probe, the more hydrogen bonding between base pairs and, in general, the higher the $T_m$. Increasing the percentage of G and C also increases the $T_m$ because G-C base pairs exhibit additional hydrogen bonding and therefore greater thermal stability than A-T base pairs. Such considerations are well known in the art. See, e.g., J. SAMBROOK ET AL., MOLECULAR CLONING: A LABORATORY MANUAL, ch. 11 (2d ed. 1989).

A preferred method for determining $T_m$ measures hybridization using the Hybridization Protection Assay (HPA) disclosed by Arnold et al., "Homogenous Protection Assay," U.S. Pat. No. 5,283,174. The $T_m$ can be measured using HPA in the following manner. Probe molecules are labeled with an acridinium ester and permitted to form probe:target hybrids in a lithium succinate buffer (0.1 M lithium succinate buffer, pH 4.7, 20 mM EDTA, 15 mM aldrithiol-2, 1.2 M LiCl, 3% (v/v) ethanol absolute, 2% (w/v) lithium lauryl sulfate) using an excess amount of target. Aliquots of the solution containing the probe:target hybrids are then diluted in the lithium succinate buffered solution and incubated for five minutes at various temperatures starting below that of the anticipated $T_m$ (typically 55° C.) and increasing in 2-5° C. increments. This solution is then diluted with a mild alkaline borate buffer (600 mM boric acid, 240 mM NaOH, 1% (v/v) TRITON® X-100 (octoxynol), pH 8.5) and incubated at an equal or lower temperature (for example 50° C.) for ten minutes.

Under these conditions the acridinium ester attached to the single-stranded probe is hydrolyzed, while the acridinium ester attached to hybridized probe is relatively protected from hydrolysis. Thus, the amount of acridinium ester remaining after hydrolysis treatment is proportional to the number of hybrid molecules. The remaining acridinium ester can be measured by monitoring the chemiluminescence produced from the remaining acridinium ester by adding hydrogen peroxide and alkali to the solution. Chemiluminescence can be measured in a luminometer, such as a LEADER® 450i luminometer (Gen-Probe Incorporated, San Diego, Calif.; Cat. No. 3200i). The resulting data is plotted as percent of maximum signal (usually from the lowest temperature) versus temperature. The $T_m$ is defined as the temperature at which 50% of the maximum signal remains. In addition to the method above, $T_m$ may be determined by isotopic methods known to those skilled in the art, such as those disclosed by Hogan in U.S. Pat. No. 5,840,488.

To ensure specificity of a probe for its target, it is preferable to design probes which hybridize only to target nucleic acid under conditions of high stringency. Only highly complementary sequences will form hybrids under conditions of high stringency. Accordingly, the stringency of the hybridization assay conditions determines the amount of complementarity needed between two sequences in order for a stable hybrid to form. Stringency should be chosen to maximize the difference in stability between the probe:target hybrid and potential probe:non-target hybrids. See SAMBROOK ET AL., supra, ch. 11.

The length of the target nucleic acid sequence region and, accordingly, the length of the probe sequence can also be important. In some cases, there may be several sequences from a particular region, varying in location and length, which may be used to design probes with the desired hybridization characteristics. In other cases, one probe may be significantly better with regard to specificity than another which differs from it merely by a single base. While it is possible for polynucleotides that are not perfectly complementary to hybridize, the longest stretch of perfectly complementary bases, as well as the base compositions, will generally determine hybrid stability.

If a target nucleic acid is wholly or partially involved in an intra-molecular or inter-molecular hybrid, it will be less able to participate in the formation of a new inter-molecular probe:target hybrid without a change in the reaction conditions. Ribosomal RNA molecules are known to form very stable intra-molecular helices and secondary structures by hydrogen bonding. By designing a probe to a region of the target nucleic acid which remains substantially single-stranded under hybridization assay conditions, the rate and extent of hybridization between probe and target may be increased. However, if the preferred target region is contained in region of an rRNA molecule which is at least partially double-stranded, then helper probes may used to facilitate access to the target region. A helper probe is a polynucleotide which is designed to hybridize to the target nucleic acid at a different locus than that of a polynucleotide probe, thereby increasing the rate of hybridization of the polynucleotide probe to the target nucleic acid, increasing the melting temperature of the probe:target hybrid, or both. Hogan et al. disclose helper probes in U.S. Pat. No. 5,030,557.

A genomic target occurs naturally in a double-stranded form, as does a product of the polymerase chain reaction (PCR) method of amplification. These double-stranded targets are naturally inhibitory to hybridization with a probe and require denaturation prior to hybridization. Appropriate denaturation and hybridization conditions are known in the art. See, e.g., Southern *J. Mol. Biol.* (1975) 98:503.

A number of formulae are available which will provide an estimate of the melting temperature for perfectly matched polynucleotides to their target nucleic acids. One such formula is the following:

$$T_m = 81.5 + 16.6(\log_{10}[Na^+]) + 0.41(\text{fraction } G+C) - (600/N)$$

(where N=the length of the polynucleotide in number of nucleotides) provides a good estimate of the $T_m$ for polynucleotides between 14 and 60 to 70 nucleotides in length. From such calculations, subsequent empirical verification or "fine tuning" of the $T_m$ may be made using screening techniques well known in the art. For further information on hybridization and polynucleotide probes, reference may be made to SAMBROOK ET AL., supra, ch. 11. This reference, among others well known in the art, also provides estimates of the effect of mismatches on the $T_m$ of a hybrid. Thus, from known nucleotide sequences, polynucleotides may be designed which can distinguish between these sequences.

C. Preparation of Polynucleotide Probes

The polynucleotide probes used in the present invention can be readily prepared by methods known in the art. Preferably, the probes are synthesized using solid phase methods. For example, Caruthers describes using standard phosphoramidite solid-phase chemistry to join nucleotides by phosphodiester linkages. See Caruthers et al. *Methods Enzymol.* (1987) 154:287. Automated solid-phase chemical synthesis using cyanoethyl phosphoramidite precursors has been described by Barone. See Barone et al. *Nucleic Acids Res.* (1984) 12(10):4051. Likewise, a procedure for synthesizing polynucleotides containing phosphorothioate linkages is disclosed by Batt, "Method and Reagent for Sulfurization of Organophosphorous Compounds," U.S. Pat. No. 5,449,769. In addition, the synthesis of polynucleotides having different linkages including methylphosphonate linkages are disclosed by Riley et al., "Process for the Purification of Oligomers," U.S. Pat. No. 5,811,538. Moreover, methods for the organic synthesis of polynucleotides are known to those of skill in the art and are disclosed by, for example, SAMBROOK ET AL., supra, ch. 11.

Following synthesis and purification of a particular polynucleotide, several different procedures may be utilized to purify and control the quality of the polynucleotide. Suitable procedures include polyacrylamide gel electrophoresis or high pressure liquid chromatography. Both of these procedures are well known to those skilled in the art.

Polynucleotides which can be used in the present invention may be modified with chemical groups to enhance their performance, provided those polynucleotides being used as probes carry a net positive charge. For example, backbone-modified polynucleotides, such as those having phosphorothioate, methylphosphonate, 2'-O-alkyl or peptide groups which render the polynucleotides resistant to the nucleolytic activity of certain polymerases or to nuclease enzymes may allow the use of such enzymes in an amplification or other reaction. Another example of a modification involves using non-nucleotide linkers incorporated between nucleotides in the nucleic acid chain of a polynucleotide, and which do not prevent hybridization of a probe. See Arnold et al., "Non-Nucleotide Linking Reagents for Nucleotide Probes," U.S. Pat. No. 6,031,091. The polynucleotides of the present invention may also contain mixtures of the desired modified and natural nucleotides.

Once synthesized, a selected polynucleotide may be labeled by any of several well known methods (see, e.g., SAMBROOK ET AL., supra, ch. 10). Useful labels include radioisotopes as well as non-radioactive reporting groups. Isotopic labels include $^3H$, $^{35}S$, $^{32}P$, $^{125}I$, $^{57}Co$ and $^{14}C$. Isotopic labels can be introduced into the polynucleotide by techniques known in the art such as nick translation, end labeling, second strand synthesis, the use of reverse transcription, and by chemical methods. When using radiolabeled probes, hybridization can be detected by autoradiography, scintillation counting or gamma counting. The detection method selected will depend upon the particular radioisotope used for labeling.

Non-isotopic materials can also be used for labeling and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups, as disclosed by Arnold et al. in U.S. Pat. No. 6,031,091. Non-isotopic labels include fluorescent molecules (individual labels or combinations of interacting labels, such as the fluorescence resonance energy transfer (FRET) pairs disclosed by Tyagi et al. in U.S. Pat. No. 5,925,517), chemiluminescent molecules, enzymes, cofactors, enzyme substrates, haptens or other ligands. The probes of the present invention are preferably labeled by means of a non-nucleotide linker with an acridinium ester (AE). Acridinium ester labeling may be performed as disclosed by Arnold et al., "Acridinium Ester Labelling and Purification of Nucleotide Probes," U.S. Pat. No. 5,185,439.

D. Polycationic Polymers

Polymers of the present invention have a net cationic charge and include polymers of one repetitive monomer type (i.e., homopolymers) as well as polymers of multiple repetitive monomer types (i.e., copolymers). Polymers of the present invention further include block and graft copolymers. Those polymers having multiple monomer types may include, in addition to cationic monomers, monomers which are ionic or anionic or both, provided the cationic charges of the polymers are in excess of the anionic charges. The cationic charges of the polymers may be localized or delocalized (i.e., localized to a particular monomer or spread over two or more contiguous monomers). In one preferred embodiment, the distance between adjacent cationic monomers of the polymers approximates the distance between adjacent phosphate groups of a polynucleotide, which is in the range of about 5 to about 7 angstroms. The polymers of the present invention are synthetic and water soluble.

The polycationic polymers of the present invention promote the reassociation or hybridization (collectively referred to herein as "association") of complementary polynucleotides by greatly increasing the rate at which polynucleotides associate in solution, even in reaction mixtures containing medium to high salt concentrations (i.e., salt concentrations greater than about 150 mM for monovalent cations, such as lithium (Li+), potassium (K+) and sodium (Na+)). Reaction mixtures having salt concentrations greater than about 5 to about 10 mM for monovalent cations are preferred in the present invention. The rate enhancement due to the presence of polycationic polymers in a reaction mixture may be as great as 2-fold, 5-fold, 10-fold, 100-fold, 1000-fold or greater. Determining the effect that any particular polycationic polymer or group of polycationic polymers has on the rate of association of complementary polynucleotides can be evaluated using reference conditions that differ only by the presence or absence of the polycationic polymer or group of polycationic polymers. The reference conditions used herein included either a high salt hybridization buffer (100 mM lithium succinate, pH 5.1, 0.35 M LiCl and 0.1% (v/v) TRITON® X-100) or a low salt hybridization buffer (100 mM lithium succinate, pH 5.1, 50 mM LiCl and 0.1% (v/v) TRITON® X-100) and an incubation temperature of 40° C. or 60° C. The reference conditions may be any conditions which facilitate stable hybridization between complementary polynucleotides. Other conditions of stringency could serve as reference conditions for determining the effect of a polycationic polymer or a group of polycationic polymers on the rate of association between complementary polynucleotides, including the standard reaction conditions of 0.18 M $Na^+$ (0.12 M sodium phosphate buffer, pH 6.8) at 60° C. See Britten et al. *Methods Enzymol.* (1974) 29:363-418.

Polycationic polymers are known to significantly increase the $T_m$ of nucleic acid duplexes, and large increases in $T_m$ are often associated with a loss in discrimination. See, e.g., Maruyama et al. *Bioconjugate Chem.* (1998) 9:292-299 and Majlessi et al. *Nucleic Acids Research* (1998) 26:2224-2229. For detection assays, in which polynucleotide probes are intended to preferentially hybridize to target nucleic acid in the presence of non-target nucleic acid, the probes must be specific for the target nucleic acid in order for the assay to be of diagnostic or probative value. A loss in discrimination cannot be tolerated. Thus, the applicant's discovery that polycationic polymers of the present invention can be used in an assay employing generally practiced salt and temperature conditions to significantly increase the $T_m$ of hybrids, without a loss in specificity for the target nucleic acid, was unexpected. The polycationic polymers of the present invention appear to function by further stabilizing the small duplex formed during nucleation, but not to such an extent that the probe loses its specificity for the target nucleic acid. (Nucleation sites have been described as spanning as few as three adjacent base pairs, and may be as long as six to eight adjacent base pairs. See Pörschke et al. *J. Mol. Biol.* (1971) 62:361-381.) As a result, the applicant surprisingly found that the polycationic polymers of the present invention can be used to increase the reaction rate of assays in which the probe preferentially hybridizes to a target nucleic acid in the presence of non-target nucleic acid, even nucleic acid from a closely related non-target organism or virus.

Through routine screening, the applicant also discovered that polycationic polymers can be selected which allow for some mismatch tolerance so that closely related strains of an organism or virus, for example, can be detected in an assay. These polymers would allow practitioners to design probes which are less sensitive to sequence variation so that multiple strains of an organism or virus could be detected with a single probe, while still having sufficient specificity to distinguish over non-target nucleic acid present in a test sample. Assays employing these selected for polymers would be particularly useful in detecting organisms or viruses exhibiting high genotypic diversity, such as the HIV-1 and HIV-2 viruses. See, e.g., Chee et al., "Array of Nucleic Acid Probes on Biological Chips for Diagnosis of HIV and Methods of Using the Same," U.S. Pat. No. 5,861,242. By adjusting the conditions of stringency (e.g., salt and temperature conditions), it is expected that these same polymers could be used in assays requiring single base mismatch discrimination.

While not wishing to be bound by theory, the applicant currently believes that the polycationic polymers of the present invention assemble in solution to form complexes of nanometer dimensions (i.e., nanoparticles) which create a charge environment that attracts negatively charged polynucleotides (e.g., polynucleotide probes and target nucleic acids) present in the solution. Once localized by these complexes, polynucleotides having sufficiently complementary sequences are able to more readily associate, thereby enhancing the association kinetics of complementary polynucleotides. Alternatively, the applicant theorizes that the polycationic polymers of the present invention assemble in solution as they bind polynucleotides, such that the polynucleotides are being localized as the nanoparticles are forming rather than after the nanoparticles have already largely formed. Microscopy methods well known to those skilled in the art could be used to screen for the formation of nanoparticles comprising polycationic polymers.

Based upon the applicant's theory that the formation of complexes attracts and concentrates polynucleotides present in a reaction mixture, it is preferable that the molar concentration of cationic monomers which are present in the polycationic polymers of the reaction mixture exceed the molar concentration of anionic phosphate groups (i.e., nucleotides) which are present in the polynucleotides of the reaction mixture. Providing a molar excess of cationic monomers to a reaction mixture should also prevent complexes of polycationic polymers from precipitating out of solution, as may occur when approximately equal numbers of cationic monomers and phosphate groups are provided to the reaction mixture. Precipitation is undesirable since nucleic acids are removed from solution, thereby impeding hybridization between complementary polynucleotides. While even small amounts of the polycationic polymers should enhance the rate of association in a reaction mixture, preferred concentrations of the polycationic polymers are in the range of about 1 µM to about 1000 µM, and more preferably in the range of about 10 µM to about 100 µM.

The weight average molecular weights ($M_w$) of polycationic polymers of the present invention are preferably less than about 300,000 Da, as polymers having a $M_w$ greater than about 300,000 Da are often too viscous or polydisperse to adequately facilitate the association of complementary polynucleotides. While the lowest acceptable $M_w$ will depend greatly upon the polymer used, polymers having a $M_w$ of at least 10,000 Da are generally preferred. Polymers having optimal $M_w$ values for enhancing the association kinetics of complementary polynucleotides can be determined through routine screening procedures for any given set of reaction conditions.

Although the polycationic polymers of the present invention may be polydisperse, it is generally preferred that the polymers of a mixture have a polydispersity value of about one. Since polydispersity is a measure of the ratio of the weight-average molecular weight and number-average molecular weight ($M_w/M_n$) in a polymer mixture, the closer this ratio is to one, the greater the size uniformity of the polymers making up the mixture.

Polycationic polymers contemplated by the present invention include, but are not limited to, poly-L-lysine (an example of which is poly-L-lysine hydrobromide available from Fluka AG of Buchs, Switzerland as Cat. Nos. 81333 and 81355), poly(lys, tyr) 4:1 (an example of which is poly(lys, tyr) 4:1 hydrobromide available from Sigma Chemical Company of St. Louis, Mo. as Product No. P 4659), poly-L-histidine (an example of which is poly-L-histidine hydrochloride available from Sigma Chemical Company as Product No. P 2534), poly-L-arginine (an example of which is poly-L-arginine hydrochloride available from Sigma Chemical Company as Product No. P 4663), hexadimethrine bromide (1,5-dimethyl-1,5-diazaundecamethylene polymethobromide) (an example of which is available from Sigma Chemical Company as Product No. H 9268), poly(allylamine hydrochloride) (an example of which is available from Aldrich Chemical Company of Milwaukee, Wis. as Cat. No. 28,321-5), poly(diallyldimethylammonium chloride) (an example of which is available from Aldrich Chemical Company as Cat. No. 40,901-4), poly[bis(2-chloroethyl)ether-alt-1,3 bis[3-(dimethyl amino)propyl]urea], polyethylenimine (an example of which is available from Aldrich Chemical Company as Cat. No. 40,872-7) and poly-L-lysine dextran. While not specifically enumerated, other polycationic polymers are envisaged by the present invention which function to enhance the association kinetics of complementary polynucleotides. Such polycationic polymers can be easily screened for by skilled artisans following the guidance provided herein without having to engage in anything more than routine experimentation.

The polycationic polymers of the present invention may be used in conjunction with other techniques for increasing reaction rates, including techniques which depend upon volume exclusion to enhance the rate of association between complementary polynucleotides. By adding synthetic polymers such as polyetheylene glycol, dextran or dextran sulfate, the volume of a reaction mixture which remains available to the polynucleotide reactants is reduced, thereby increasing the effective concentration of these reactants. Volume exclusion techniques are well known in the art and are described in, for example, Renz et al. *Nucleic Acids Res.* (1984) 12:3435-3444 and Wahl et al. *Proc. Natl. Acad. Sci. USA* (1979) 75:3683-3687. Other techniques for increasing the rate of association between polynucleotides which may be used in combination with the polymers of the present invention could include techniques which enhance reaction rates by including a precipitating agent. See, e.g., Kohne et al., "Accelerated Nucleic Acid Reassociation Method," U.S. Pat. No. 5,132,207.

E. Association Kinetics

The term "association rate," as used herein, refers to the rate at which two polynucleotides reassociate or hybridize to form a duplex in solution. A number of factors affect the association rate, including the size and concentration of the polynucleotides, the incubation temperature and the salt concentration of the reaction mixture. Conventionally, association rates have been quantified using the $C_ot$ analysis developed by Britten and Kohne. *Science* (1968) 161:529-540. Following this analysis, the fraction of single-stranded polynucleotides remaining at any time during an isothermal reaction is given by the formula: $C/C_o=1/(1+kC_ot)$, where $C_o$ is the starting concentration of the polynucleotides in nucleotides per liter, C is the concentration of the polynucleotides in nucleotides per liter remaining at any given time, t is the time of the reaction (s), and k is the rate constant for a second-order reaction ($M^{-1}s^{-1}$). When a reaction is half complete (time=$t_{1/2}$), $C/C_o=½$ and $C_ot_{1/2}=1/k$. Thus, $C_ot_{1/2}$ is inversely proportional to the rate constant and is a measure of the association rate.

A shortcoming of the $C_ot$ analysis method for measuring association rates is that it does not account for the simultaneous dissociation of polynucleotides during a reaction. The amount of dissociation that takes place during a reaction will depend on such factors as the temperature of the reaction, as it relates to the melting temperature of the duplex formed between polynucleotides, and the time of the reaction. As the reaction temperature approaches the melting temperature of the duplex or as the reaction period increases, the amount of dissociation is expected to rise. Therefore, to accurately calculate the rate of association, it is necessary to factor in both the association rate constant and the dissociation rate constant of the reaction.

Figure 2:
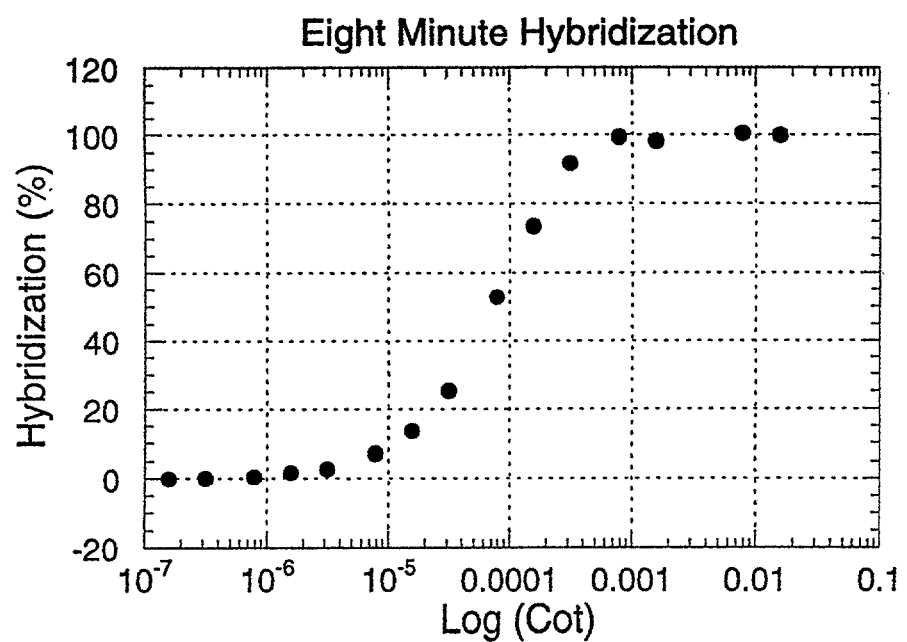
FIG. 2 is a plot of percent hybridization versus log of $C_o t$ for a range of target concentrations used to determine the rate of a reaction having an eight minute incubation period, where each (●) represents a data point derived from experimental data.

To make this determination, the applicant devised a novel equation and method for calculating a rate constant for measuring the rate of a reaction which accounts for both association and dissociation of the involved polynucleotides. The first step in this procedure is to plot percent hybridization versus log of $C_ot$ data points on a graph for each of the polynucleotide concentrations tested. Examples of such plots are depicted in FIGS. 1 and 2, which plot data points (●) calculated from the experimental data of Example 1 infra. These graphs plot data points for hybridizations of both 3 and 8 minutes. Two incubation periods are used to ensure that the association of polynucleotides is increasing with time so that it can be established that the rate being calculated is a kinetic determination and not an equilibrium measurement. An increase in the percentage of hybridization can be demonstrated by showing that the percentage of hybridization is increasing with both concentration and time.

Figure 3:
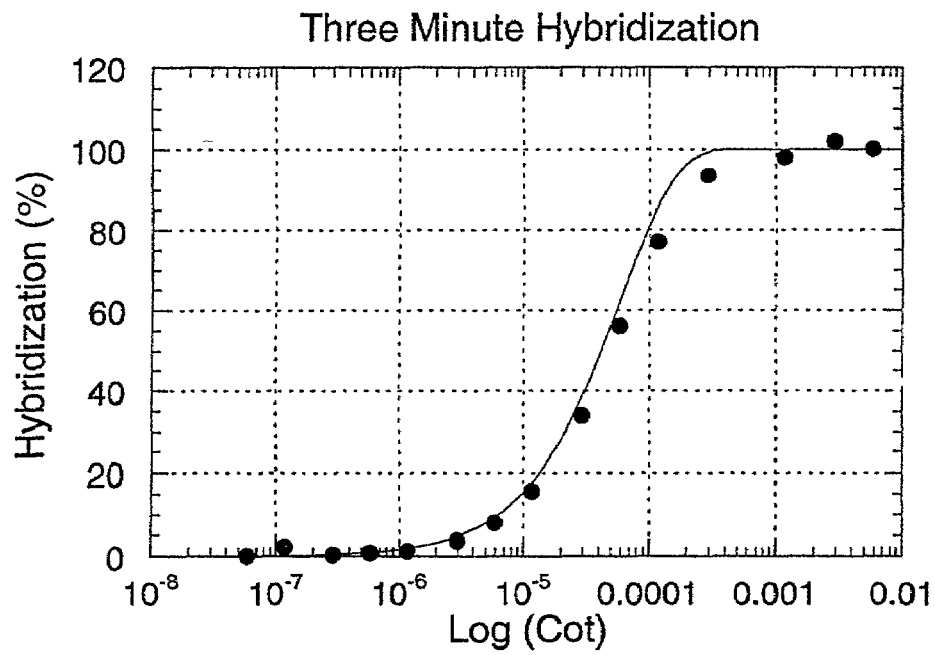
FIG. 3 is a plot of the predicted percent hybridization versus log of $C_o t$ curve (where the estimated association rate constant $(k_1)=16,000$ $M^{-1}$ and the estimated dissociation rate constant $(k_2)=0$) superimposed over the plotted data points (●) derived from experimental data and depicted in FIG. 1.
Figure 4:
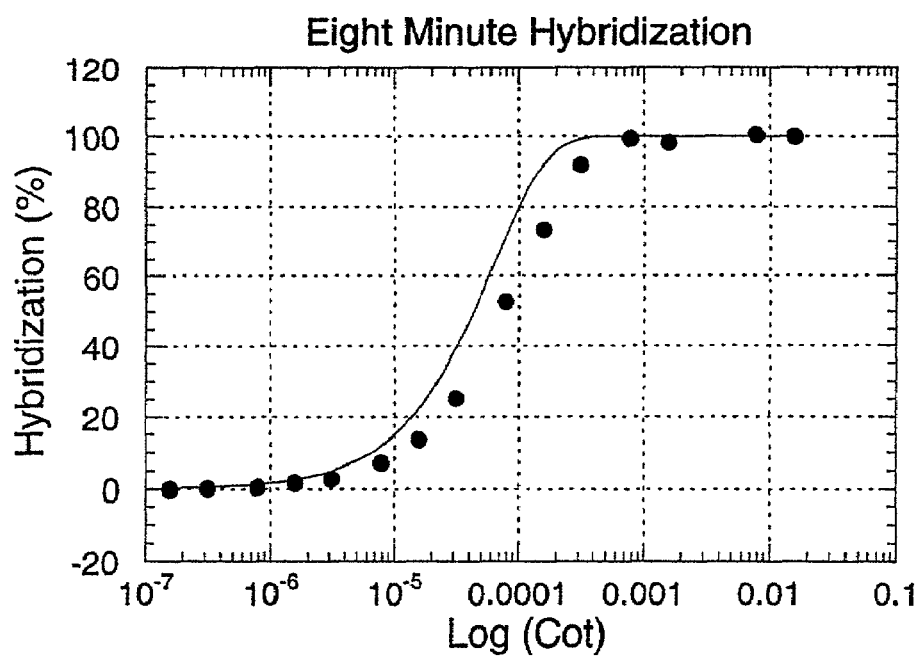
FIG. 4 is a plot of the predicted percent hybridization versus log of $C_o t$ curve (where the estimated $k_1=16,000$ $M^{-1}$ and the estimated $k_2=0$) superimposed over the plotted data points (●) derived from experimental data and depicted in FIG. 2.

Next, predicted curves are plotted based on percent hybridization values calculated from the following novel equation: % hybridization=$100(1-K)(1-\exp-(k_1C_o+k_2)t)$, where $K=k_2/(C_ok_1+k_2)$, t=time (s), $C_o$=initial concentration of polynucleotides in nucleotides (M), $k_1$=the association rate constant ($M^{-1}s^{-1}$), and $k_2$=the dissociation rate constant ($s^{-1}$). Both $k_1$ and $k_2$ are unknowns in this equation and are estimated by the practitioner. To begin the analysis, $k_1$ is assigned a rate constant value derived from a conventional $C_ot$ analysis and $k_2$ is assigned a rate constant value of zero, which presupposes that there was no dissociation during the reaction. (When $k_2$=0, this equation reduces to the $C_ot$ equation.) Plugging the actual t values and estimated $k_1$ and $k_2$ values into the new equation, curve plotting software, such as KaleidaGraph 3.0 (Synergy Software; Reading, Pa.), can be used to generate a curve which relates percent hybridization and $C_o$ across a range of concentrations tested. Examples of such curves are depicted in FIGS. 3 and 4, which superimpose the curves generated using the curve plotting software over the plotted data points (●) derived from the $C_ot$ analysis and depicted in FIGS. 1 and 2. (For FIGS. 3 and 4, a $k_1$ rate constant of 16,000 $M^{-1}s^{-1}$ and a $k_2$ rate constant of 0 were fitted into the equation.) As can be seen from FIGS. 3 and 4, the curves and plotted data points in each of these graphs are not entirely coincident.

Figure 5:
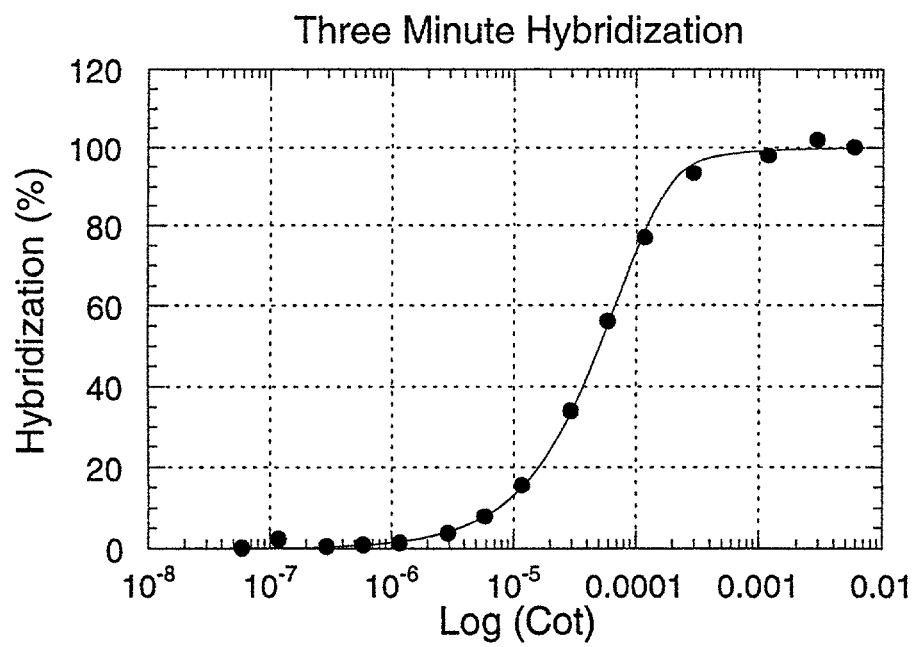
FIG. 5 graphically represents an adjustment to $k_1$ and $k_2$ ($k_1=14,500$ $M^{-1}s^{-1}$ and $k_2=8.33\times10^{-4}s^{-1}$), such that the predicted curve of FIG. 3 and the data points (●) of FIG. 1 are coincident. Adjusted $k_1$ and $k_2$ should provide a closer approximation of the actual rate of this reaction.
Figure 6:
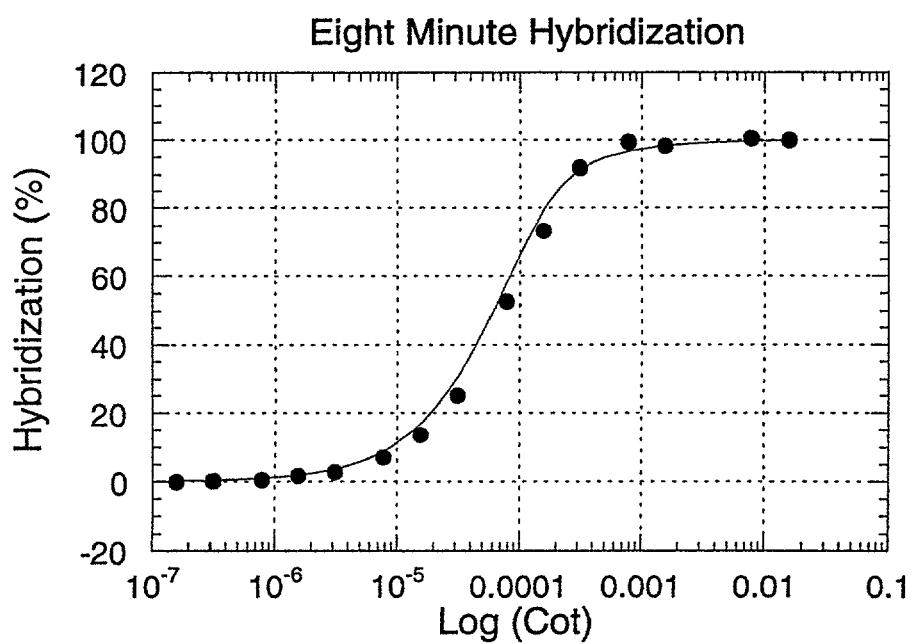
FIG. 6 graphically represents an adjustment to $k_1$ and $k_2$ ($k_1=14,500$ $M^{-1}s^{-1}$ and $k_2=8.33\times10^{-4}s^{-1}$), such that the predicted curve of FIG. 4 and the data points (●) of FIG. 2 are coincident. Adjusted $k_1$ and $k_2$ should provide a closer approximation of the actual rate of this reaction.

Finally, $k_1$ and $k_2$ are adjusted until the plotted data points from the experimental data are coincident with the curves plotted from the new equation using the curve plotting software. FIGS. 5 and 6 show the graphs of FIGS. 3 and 4 after $k_1$ and $k_2$ have been adjusted, resulting in a curve and plotted data points (●) which coincide in each graph. (To obtain a coincident curve and plotted data points for each of these graphs, $k_1$ was adjusted to 14,500 $M^{-1}s^{-1}$ and $k_2$ was adjusted to $8.33 \times 10^{-4}$ $s^{-1}$.) When two incubation periods are used, as in the example represented in FIGS. 1-6, $k_1$ and $k_2$ must be the same for both reactions to ensure that the amount of dissociation is being accurately accounted for in arriving at a final association rate constant ($k_1$). As stated above, one reason for testing two association periods is that the association and dissociation of polynucleotides tend to increase over time of reaction. Thus, data for two distinct reaction times results in a more accurate determination of the rate of association.

Figure 7:
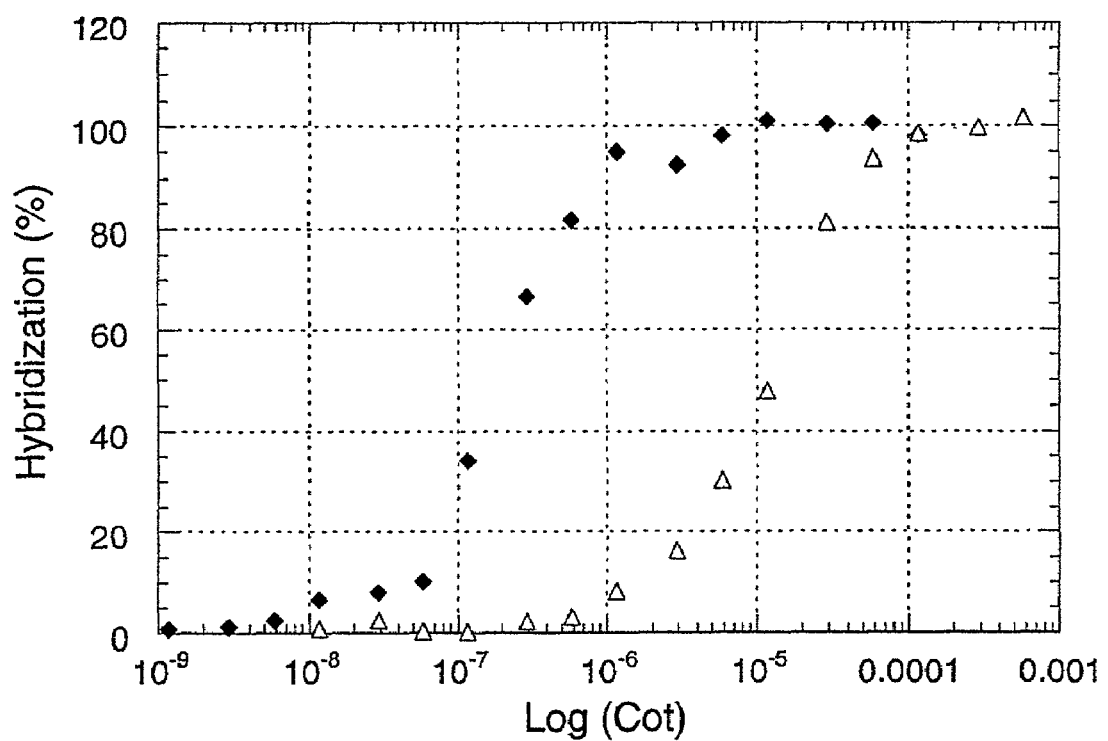
FIG. 7 is a plot of percent hybridization versus log of $C_o t$ for a range of target concentrations with polymer (♦) and without polymer (Δ), where each (♦) and (Δ) represents a data point derived from experimental data.

Either the conventional $C_ot$ analysis or the new equation and curve plotting procedure described above may be used to determine the extent to which any particular polycationic polymer or group of polycationic polymers enhance the rate of association for a set of polynucleotides. While the latter is preferred for quantitative reasons, both methods will provide a qualitative measure of whether a polycationic polymer or group of polycationic polymers positively affect the kinetics of an association reaction. This is demonstrated in FIG. 7, which directly compares percent of hybridization versus log of $C_ot$ for poly-L-histidine hydrochloride (♦) and no polymer (Δ) under identical hybridization conditions based on data from Example 1 infra. It will be understood, however, that both equations are estimates of actual association rates, which become more difficult to calculate with accuracy as association rates increase.

F. Detection Systems

Before a target nucleic acid can be detected in a test sample, it must be made available in the reaction mixture for hybridization to a polynucleotide probe. Many cellular disruption methods for releasing nucleic acid into a reaction mixture are well known in the art, and include both chemical and enzymatic methods, as well as mechanical means such as ultrasonication, agitation with glass beads, grinding with abrasives and the French pressure cell. Other methods involve weakening the cell wall by one or more rounds of freezing and thawing or by treatment with a lysing enzyme such as lysozyme, followed by dissolution of the cell membrane by treatment with a strong detergent or a chaotropic reagent (i.e., a reagent that disrupts hydrophobic interactions). The lysate of these methods include organelles, proteins (including enzymes such as proteases and nucleases), carbohydrates, and lipids as well as nucleic acids, which may require further purification of the nucleic acids.

An extraction method requiring only a single reagent to release nucleic acids from a wide range of cellular types in a form suitable for nucleic acid hybridization without the need for subsequent purification steps is disclosed by Clark et al., "Method for Extracting Nucleic Acids from a Wide Range of Organisms," U.S. Pat. No. 5,786,208. This extraction method combines a test sample with a reagent which includes a non-ionic detergent, an optional anionic detergent and a metal chelating agent and heats the resulting mixture at a temperature between 80° and 100° C. until nucleic acids are released from the cells. Because anionic detergents such as lithium lauryl sulfate are believed to disrupt or denature nucleases (e.g., ribonucleases) present in the test sample, inclusion of an anionic detergent is particularly desirable when the target nucleic acid is RNA. (In this and other extraction methods employing an anionic detergent, the target nucleic acid is preferably separated from the anionic detergent prior to contacting the target nucleic acid with the polycationic polymers of the present invention.) Nucleic acids are released in this method without observable destruction to cell walls, so that the liberated nucleic acids are suitable for hybridization, amplification or other genetic manipulations without further purification.

Following sample preparation, the polycationic polymers of the present invention may be used in a variety of detection systems, including both heterogenous and homogenous systems used to determine the presence or amount of target nucleic acids in a sample. In a heterogenous assay, a step is required to isolate or separate probe:target hybrids from excess probe sequences before single-stranded probes and probe:target hybrids can be distinguished from each other. Examples of heterogenous assay systems are disclosed by, for example, Ranki et al. in U.S. Pat. No. 4,486,539 and Stabinsky in U.S. Pat. No. 4,751,177. Homogenous assays on the other hand require no separation step, thereby permitting the in solution detection of probe:target hybrids in the presence of excess probe sequences. Examples of detection systems which can be used in either the heterogenous or homogenous systems are the Hybridization Protection Assay and the Adduct Protection Assay disclosed by Arnold et al. in U.S. Pat. No. 5,283,174, and Becker et al., "Adduct Protection Assay," U.S. Pat. No. 5,731,148, respectively. Other well known detection systems employ self-hybridizing probes which incorporate interacting labels that emit differentially detectable signals, depending upon whether the probes are bound to target nucleic acid or remain self-hybridized in the reaction mixture. See, e.g., Bagwell in U.S. Pat. No. 5,607,834; Tyagi et al. in U.S. Pat. No. 5,925,517; and Becker et al. in U.S. Pat. No. 6,361,945.

The Hybridization Protection Assay is a particularly preferred homogenous detection system based on differential hydrolysis. See Arnold et al. in U.S. Pat. No. 5,283,174; see also Arnold et al. *Clinical Chemistry* (1989) 35:1588-1594. In this detection system, an excess of probe labeled with a chemiluminescent acridinium ester is provided to a test sample for a period of time and under conditions permitting the probe to stably hybridize to a target nucleic acid suspected of being present in the test sample. Following hybridization, acridinium ester label associated with unhybridized probe is selectively degraded by providing an alkaline reagent to the test sample which hydrolyzes of the phenyl ester of the acridinium ester. Label associated with hybridized probe is protected from hydrolysis by intercalation of the label in the duplexed molecule. Thus, the amount of acridinium ester remaining in the test sample is proportional to the amount of hybrid and can be measured by the chemiluminescence produced from acridinium ester labels associated with hybridized probe upon the addition of hydrogen peroxide followed by alkali. Chemiluminescence can be measured in a luminometer, including the LEADER® 450i luminometer. Useful HPA conditions and reagents are exemplified in Example 1 below.

The adduct protection assay, which is preferred when measuring hybridization kinetics, can facilitate the detection of a target polynucleotide by exploiting adduct formation to preferentially alter signal production from a label present on a polynucleotide probe not bound to the target polynucleotide. The assay involves the formation of a protective micro-environment when a labeled polynucleotide probe forms a duplex with the target polynucleotide. Label associated with probe bound to target polynucleotide is preferentially protected from forming an adduct with a signal altering ligand, such as sodium sulfite. Label associated with free probe, however, can be selectively altered in the presence of the signal altering ligand, thereby affecting its ability to produce a detectable signal. Examples of signal altering ligands useful in an adduct protection assay include tetrahydrothiopene, propanethiol, benzylmercaptan, sulfite, glycol sulfite, hydrosulfite, metabisulfite, thiosulfate, thiophosphate, metaarsenite, tellurite, arsenite and thiocyanate. By introducing a signal triggering reagent which causes label to produce a detectable signal, the presence or amount of a probe:target duplex in a sample can be determined. The preferred label is a chemiluminescent reagent, such as an acridinium ester, and the preferred signal triggering reagent is sodium hydroxide or hydrogen peroxide. Acridinium ester labels and means for their detection are disclosed by Arnold et al. in U.S. Pat. No. 5,185,439.

Before signal triggering reagent is introduced into the sample, polycationic polymers and polynucleotides are first dissociated from each other in the preferred adduct protection assay. (A dissociation step is not required for all embodiments of the present invention.) Dissociation of polycationic polymers from polynucleotides can be effected with anionic detergents and polyanions which weaken the binding of polycations to nucleic acids (e.g., polyglutamic acid, polyaspartic acid, sodium dodecyl sulfate and polynucleotides). For this reason, where a dissociation step is to be included, the sample should exclude appreciable amounts of anionic detergents and polyanions capable of dissociating polycationic polymers from polynucleotides prior to the dissociation step so that the enhanced association of complementary polynucleotides in the presence of polycationic polymers can proceed unimpeded. More particularly, the total anionic charge in the reaction mixture should be less than the total cationic charge. A preferred dissociating reagent is lithium lauryl sulfate (LLS) at a final concentration of about 1% (w/v) in the reaction mixture.

Prior to detection, it may be desirable to increase the quantity of target nucleic acid present, and thus the sensitivity of the assay, by exposing the reaction mixture to nucleic acid amplification conditions. Under amplification conditions, polynucleotide chains containing the target sequence or its complement are synthesized in a template-dependent manner from ribonucleoside or deoxynucleoside triphosphates using nucleotidyltransferases known as polymerases. There are many amplification procedures in common use today, including the polymerase chain reaction (PCR), Q-beta replicase, self-sustained sequence replication (3SR), transcription-mediated amplification (TMA), nucleic acid sequence-based amplification (NASBA), ligase chain reaction (LCR), strand displacement amplification (SDA) and loop-mediated isothermal amplification (LAMP), each of which is well known in the art. See, e.g., Mullis, "Process for Amplifying Nucleic Acid Sequences," U.S. Pat. No. 4,683,202; Erlich et al., "Kits for Amplifying and Detecting Nucleic Acid Sequences," U.S. Pat. No. 6,197,563; Walker et al. *Nucleic Acids Res.* (1992) 20:1691-1696; Fahy et al. *PCR Methods and Applications* (1991) 1:25-33; Kacian et al., U.S. Pat. No. 5,399,491; Kacian et al., "Nucleic Acid Sequence Amplification Methods," U.S. Pat. No. 5,480,784; Davey et al., "Nucleic Acid Amplification Process," U.S. Pat. No. 5,554,517; Birkenmeyer et al., "Amplification of Target Nucleic Acids Using Gap Filling Ligase Chain Reaction," U.S. Pat. No. 5,427,930; Marshall et al., "Amplification of RNA Sequences Using the Ligase Chain Reaction," U.S. Pat. No. 5,686,272; Walker, "Strand Displacement Amplification," U.S. Pat. No. 5,712,124; Notomi et al., "Process for Synthesizing Nucleic Acid," European Patent Application No. 1 020 534 A1; Dattagupta et al., "Isothermal Strand Displacement Amplification," U.S. Pat. No. 6,214,587; and HELEN H. LEE ET AL., NUCLEIC ACID AMPLIFICATION TECHNOLOGIES: APPLICATION TO DISEASE DIAGNOSIS (1997).

A preferred method for amplifying a target sequence is transcription-mediated amplification (TMA). See, e.g., Kacian et al. in U.S. Pat. Nos. 5,399,491 and 5,480,784 and LEE ET AL., supra, ch. 8. TMA is an isothermal amplification procedure which allows for a greater than one billion-fold increase in copy number of the target sequence using reverse transcriptase and RNA polymerase. The target sequence in a TMA amplification may be any type of nucleic acid, including rRNA, mRNA or DNA. TMA reaction involves converting a single-stranded target sequence to a double-stranded DNA intermediate by reverse transcriptase in the presence of a sense primer and an antisense primer having a 5' RNA polymerase-specific promoter sequence (i.e., promoter-primer). Reverse transcriptase creates a DNA copy of the target sequence by extension from the 3' end of the promoter-primer in the presence of nucleoside triphosphate substrates. Where the target sequence is RNA, the RNA in the resulting DNA:RNA duplex is degraded by RNase H activities of reverse transcriptase. The sense primer then binds to the DNA copy, and a new strand of DNA is synthesized from the 3' end of the sense primer by reverse transcriptase, thereby creating a double-stranded DNA intermediate molecule. Included in this DNA intermediate is a double-stranded promoter sequence which is recognized by RNA polymerase and transcribed into hundreds of copies of RNA. Each of these transcribed RNA molecules, in turn, can be converted to a double-stranded DNA intermediate which is used for producing additional RNA. Thus, TMA reactions proceed exponentially. Particular parameters of a TMA reaction, including concentrations of enzymes, primers and nucleoside triphosphates, as well as reaction times and temperatures, can be determined and adapted from what is well known in the art about TMA reactions without having to engage in undue experimentation.

If the detection step is preceded by an amplification step, the target nucleic acid is preferably isolated and purified before amplifying the target sequence. A wide variety of procedures for isolating and purifying a target nucleic acid are well known in the art.

A particularly preferred method for isolating and purifying a target nucleic acid prior to amplification is disclosed by Weisberg et al. in U.S. Pat. No. 6,280,952. In this system, the capture probe hybridizes to the target nucleic acid and an immobilized probe hybridizes to the capture probe:target complex under different hybridization conditions. Under a first set of hybridization conditions, hybridization of the capture probe to the target nucleic acid is favored over hybridization of the capture probe to the immobilized probe. Thus, under this first set of conditions, the capture probe is in solution rather than bound to a solid support, thereby maximizing the concentration of the free capture probe and utilizing favorable liquid phase kinetics for hybridization to the target nucleic acid. Polycationic polymers of the present invention may be provided to the reaction mixture under this first set of conditions to promote rapid hybridization of the capture probe to the target nucleic acid. After the capture probe has had sufficient time to hybridize to the target nucleic acid, a second set of hybridization conditions is imposed permitting in the capture probe:target complex to hybridize to the immobilized probe, thereby isolating the target nucleic acid in the sample solution. The immobilized target nucleic acid may then be purified, and a target sequence present in the target nucleic acid may be amplified and detected. A purification procedure which includes one or more wash steps is generally desirable when working with crude samples (e.g., clinical, environmental, industrial, food, water, etc.) to prevent enzyme inhibition and/or nucleic acid degradation due to substances present in the sample.

Instrument systems for performing detection assays are well known in the art and may be used to perform manual, semi-automated or fully automated assays. Some of these instrument systems are limited to direct detection (no prior amplification step), while others have the capability of performing both amplification and detection. These instrument systems may detect the formation of polynucleotide hybrids using any of a variety of techniques known in the art including, but not limited to, those based on light emission, mass, changes, changes in conductivity or turbidity. Examples of instrument systems which could be readily adapted to perform assays incorporating the polycationic polymers of the present invention in order to enhance reaction rates include those sold under the trade names of DTS 400 (detection only) and DTS 1600 (amplification and detection) by Gen-Probe Incorporated of San Diego, Calif., which represent embodiments of instrument systems disclosed by Acosta et al., "Assay Work Station," U.S. Pat. No. 6,254,826, and by Ammann et al., "Automated Process for Isolating and Amplifying a Target Nucleic Acid Sequence," U.S. Pat. No. 6,335,166.

G. Kits

The present invention also contemplates detection systems in kit form. Kits of the present invention include, in an amount sufficient for at least one assay, a polynucleotide probe which preferentially hybridizes to a target nucleic acid sequence in a test sample under hybridization assay conditions and a synthetic polycationic polymer in an amount sufficient to increase the association rate of the probe and the target sequence in the test sample under the hybridization assay conditions. The probe and the polymer may be combined in the same or separate containers. Kits containing multiple probes are also contemplated by the present invention where the multiple probes are designed to target different nucleic acid sequences and may include distinct labels which permit the probes to be differentially detected in a test sample. Kits according to the present invention may further comprise at least one of the following: (i) a reagent in an amount sufficient to dissociate the polymer from the probe in the test sample; (ii) one or more amplification primers for amplifying a target sequence contained in or derived from the target nucleic acid; (iii) a capture probe for isolating and purifying target nucleic acid present in a test sample; and (iv) if a capture probe is included, a solid support material (e.g., magnetically responsive particles) for immobilizing the capture probe, either directly or indirectly, in a test sample. Kits of the present invention may further include one or more helper probes.

Typically, the kits will also include instructions recorded in a tangible form (e.g., contained on paper or an electronic medium) for using the packaged probe and polymer in a detection assay for determining the presence or amount of a target nucleic acid sequence in a test sample. The assay described in the written instructions may include steps for isolating and purifying the target nucleic acid prior to detection with the polynucleotide probe, amplifying a target sequence contained in the target nucleic acid, and/or dissociating the probe from the polymer using a dissociating reagent. The detection assay may be diagnostic for the presence of a particular virus or organism or group of viruses or organisms, disease or condition, or it may be useful for determining a disease state or level of gene expression or for detecting the presence of a mutation or polymorphism.

The various components of the detection systems may be provided in a variety of forms. For example, the probe and/or polycationic polymer may be provided as lyophilized reagents. The lyophilized reagents may be pre-mixed before lyophilization so that when reconstituted they form a complete mixture with the proper ratio of each of the components ready for use in the assay. In addition, the detection systems of the present invention may contain a reconstitution reagent for reconstituting the lyophilized reagents of the kit. Preferred kits contain lyophilized probe reagents.

Typical packaging materials include solid matrices, such as glass, plastic, paper, foil, micro-particles and the like, which are capable of holding within fixed limits the probe, polycationic polymer and other optional reagents of the present invention. Thus, for example, the packaging materials can include glass vials used to contain sub-milligram quantities of a contemplated probe or polycationic polymer, or they can be microtiter plate wells to which probes of the present invention have been operatively affixed, i.e., linked so as to be capable of participating in a procedure for detecting a target nucleic acid sequence.

The instructions will typically indicate the reagents and/or concentrations of reagents and at least one assay method parameter which might be, for example, the relative amounts of reagents to use per amount of sample. In addition, such specifics as maintenance, time periods, temperature and buffer conditions may also be included.

EXAMPLES

Examples are provided below illustrating different aspects and embodiments of the invention. Skilled artisans will appreciate that these examples are not intended to limit the invention to the specific embodiments described therein.

Example 1

Effect of Polycationic Polymers on Hybridization Kinetics Between Perfectly Complementary Probe and Target Sequences This example shows the effect that various polycationic polymers had on the rate at which a polynucleotide probe and a perfectly complementary synthetic target sequence associated under different combinations of salt and temperature conditions. For this example, the probe had the nucleotide base sequence of SEQ ID NO:1 gctcgttgcgggactt(*)aacccaacat, which was synthesized to include a non-nucleotide linker (the asterik indicates the location of the non-nucleotide linker), as disclosed by Arnold et al. in U.S. Pat. No. 6,031,091. The probe was labeled with a chemiluminescent acridinium ester (standard AE), as disclosed by Arnold et al. in U.S. Pat. No. 5,185,439, and measured in relative light units (RLU).

The following five polymers were tested in this example, and each polymer was indicated to have the noted properties by the supplier:

(i) Poly-L-lysine hydrobromide. This polymer was purchased from Fluka AG (Cat. No. 81333; Lot No. 307943/1 497) and was indicated to have a $M_w$ of between 20,000 and 30,000 Da ("Low $M_w$Poly-L-lysine");

(ii) Poly-L-lysine hydrobromide. This polymer was purchased from Fluka AG (Cat. No. 81355; Lot No. 299299/1 1093) and was indicated to have a $M_w$ of between 150,000 and 300,000 Da ("High $M_w$Poly-L-lysine");

(iii) Poly (lys, tyr) 4:1. This polymer was purchased from Sigma Chemical Company (Product No. P 4659; Lot No. 81H5520) and was indicated to have a $M_w$ of 24,600 Da (visible) and a degree of polymerization of 123 (visible);

(iv) Poly-L-histidine hydrochloride. This polymer was purchased from Sigma Chemical Company (Product No. P 2534; Lot No. 118H5905) and was indicated to have a $M_w$ of 15,800 Da (using low angle laser light scattering) and a degree of polymerization of 91 (using low angle laser light scattering);

(v) Poly-L-arginine hydrochloride. This polymer was purchased from Sigma Chemical Company (Product No. P 4663; Lot No. 87H5903) and was indicated to have a $M_w$ of 11,800 Da (visible) and 8,400 Da (using low angle laser light scattering), a degree of polymerization of 43 (using low angle laser light scattering), and a $M_w/M_n$ of 1.25 (using low angle laser light scattering with size exclusion chromatography); and (vi) Hexadimethrine bromide. This polymer (1,5-dimethyl-1,5-diazaundecamethylene polymethobromide) was purchased from Sigma Chemical Company (Product No. H 9268; Lot No. 50K3672).

For each polymer, a total of 40 12×75 mm polypropylene tubes (Gen-Probe Incorporated; Cat. No. 2440) were set up, and each tube received 0.5 fmol probe and 20 µM polymer dissolved in 40 µl hybridization buffer. A no polymer control set was also tested in 40 12×75 mm polypropylene tubes (Gen-Probe Incorporated; Cat. No. 2440) which received only 0.5 fmol probe dissolved in 40 µl hybridization buffer. The hybridization buffer was either a high salt hybridization buffer made up of 200 mM lithium succinate, pH 5.1, 0.70 M LiCl and 0.2% (v/v) TRITON® X-100 or a low salt hybridization buffer made up of 200 mM lithium succinate, pH 5.1, 100 mM LiCl and 0.2% (v/v) TRITON® X-100. The tubes were divided into two groups of 20 tubes each and all tubes were pre-heated to 40° C. or 60° C. (consistent with the hybridization temperature indicated below) for two minutes in a circulating water bath (Lauda Dr. R. Wobser GmbH & Co. KG, Lauda-Koenigshofen, Germany; Model No. E100). With the exception of 4 control tubes for determining background RLU values in each group, 40 µl filtered water (Millipore Corporation; Bedford, Mass.; Milli-Q UF Plus; Cat. No. ZD5311595) containing synthetic RNA target sequence was added to the tubes of both groups and the tubes were mixed briefly by hand. The amount of target sequence in the 16 target-containing tubes of each group ranged (in increasing concentrations) from as low as 0.05 fmol to as high as 100,000 fmol. Precise target sequence concentrations for individual tubes are indicated in Tables 1 and 2 below. The target sequence used in this example was the RNA complement of the probe (SEQ ID NO:2 auguugguuaagucccgcaacgagc).

After adding the target sequence, the tubes of groups one and two were heated to 40° C. or 60° C. in a circulating water bath (Lauda Dr. R. Wobser GmbH & Co. KG; Model No. E100) to allow hybridization of the probe to the target sequence. The incubation time was three minutes for the tubes of group one and eight minutes for the tubes of group two. Following hybridization, lithium lauryl sulfate (LLS) was added to all of the tubes to dissociate polymer from probe. The final concentration of the LLS was 1% (w/v) for all tubes. The tubes were then placed in an ice water bath for approximately five minutes to arrest the hybridization reaction. All tubes were then analyzed in a LEADER® 50 luminometer (Gen-Probe Incorporated; Cat. No. 3100) equipped with automatic injection of detection reagents comprised of Detect Reagent I, which contained 0.14 M sodium sulfite and 0.042 M sodium borate, and Detect Reagent II, which contained 1.5 M sodium hydroxide and 0.12% (v/v) sodium peroxide. A 12 second pause was introduced between injections of the two Detect Reagents.

To determine the rate of association for no polymer and each polymer tested, the novel equation and method for calculating rate constants described in the Association Kinetics section supra were followed. Following this approach, the first step was to determine the $C_o t$ value and the percent hybridization for each concentration of target tested for each incubation period. Percent hybridizations were determined by dividing the net RLU for each target concentration by the RLU observed at high target concentrations where hybridization was complete. The net RLU for each target concentration was determined by subtracting the average background RLU observed in the four blank tubes for each test performed from the raw RLU for each target concentration. Each of these values is set forth in Tables 1 and 2 below for the no polymer 3 and 8 minute incubations tested in the low salt hybridization buffer at 40° C. (The values determined for each of the polymers tested, as well as no polymer tested in the high salt hybridization buffer at 60° C., are not shown in Tables 1 and 2.) The percent hybridization versus the log of $C_o t$ data points (●) were then plotted on the graphs, which are shown in FIGS. 1 and 2 for the no polymer 3 and 8 minute incubations.

Predicted graphs of percent hybridization versus the log of $C_o t$ were then determined based on percent hybridization values calculated using the following equation: % hybridization=$100(1-K)(1-\exp-(k_1 C_o + k_2)t)$, where $K=k_2/(C_o k_1 + k_2)$, t=time (s), $C_o$=initial concentration of polynucleotides in nucleotides (M), $k_1$=the association rate constant ($M^{-1} s^{-1}$), and $k_2$=the dissociation rate constant ($s^{-1}$). Being unknowns, $k_1$ and $k_2$ were initially assigned estimated values. The estimated $k_1$ values were determined using the conventional $C_o t$ analysis discussed in the Association Kinetics section supra (e.g., $k_1$ was determined to be 16,000 $M^{-1} s^{-1}$ by conventional $C_o t$ analysis for the no polymer tests illustrated) and the estimated value of $k_2$ was always zero. After plugging the actual t values and the estimated $k_1$ and $k_2$ values for each test performed into the equation above, KaleidaGraph 3.0 software was used to generate curves which related percent hybridization and $C_o$ across the range of target concentrations tested. The curves generated in this manner for the no polymer 3 and 8 minute incubations are depicted in FIGS. 3 and 4, where the predicted curves are shown superimposed over the graphs plotted from the experimental data and shown in FIGS. 1 and 2. The greater discrepancy between the predicted curve and the plotted data points observed at 8 minutes versus 3 minutes for each test indicated a $k_2$ that was greater than zero.

For this reason, the $k_1$ and $k_2$ values were adjusted for each test until the data points plotted from the experimental data were coincident with the curves plotted from the above new equation using the curve plotting software, as shown in FIGS. 5 and 6. Thus, the final $k_1$ and $k_2$ values for each test were the same for both incubation times, thereby ensuring that the concomitant dissociation of polynucleotides over time was being accounted for in the $k_1$ determination. Rate constants determined in this manner are set forth in Table 3 below for no polymer and each of the polymers tested.

TABLE 1

$C_0 t$ Values and Percent Hybridization for Various Concentrations of Target After a Three Minute Incubation in a Low Salt Hybridization Buffer at 40° C. in the Absence of Polymer

| Target (fmol) | $C_0 t$ ($M^{-1}s^{-1}$) | Raw RLU | Net RLU | Percent Hybridization |
|---|---|---|---|---|
| 0 | 0 | 1526 | 0 | 0 |
| 1 | $5.85 \times 10^{-8}$ | 1607 | 81 | 0.15 |
| 2 | $1.17 \times 10^{-7}$ | 2727 | 1201 | 2.26 |
| 5 | $2.93 \times 10^{-7}$ | 1791 | 265 | 0.50 |
| 10 | $5.85 \times 10^{-7}$ | 2026 | 500 | 0.94 |
| 20 | $1.17 \times 10^{-6}$ | 2289 | 763 | 1.44 |
| 50 | $2.93 \times 10^{-6}$ | 3526 | 2000 | 3.77 |
| 100 | $5.85 \times 10^{-6}$ | 5730 | 4204 | 7.93 |
| 200 | $1.17 \times 10^{-5}$ | 9850 | 8324 | 15.69 |
| 500 | $2.93 \times 10^{-5}$ | 19,545 | 18,019 | 33.97 |
| 1000 | $5.85 \times 10^{-5}$ | 31,340 | 29,814 | 56.21 |
| 2000 | $1.17 \times 10^{-4}$ | 42,403 | 40,877 | 77.07 |
| 5000 | $2.93 \times 10^{-4}$ | 51,067 | 49,541 | 93.40 |
| 20,000 | $1.17 \times 10^{-3}$ | 53,460 | 51,934 | 97.92 |
| 50,000 | $2.93 \times 10^{-3}$ | 55,629 | 54,103 | 102.01 |
| 100,000 | $5.85 \times 10^{-3}$ | 54,607 | 53,081 | 100.08 |

TABLE 2

$C_0 t$ Values and Percent Hybridization for Various Concentrations of Target After An Eight Three Minute Incubation in a Low Salt Hybridization Buffer at 40° C. in the Absence of Polymer

| Target (fmol) | $C_0 t$ ($M^{-1}s^{-1}$) | Raw RLU | Net RLU | Percent Hybridization |
|---|---|---|---|---|
| 0 | 0 | 1641 | 0 | 0 |
| 1 | $1.56 \times 10^{-7}$ | 1605 | -36 | -0.07 |
| 2 | $3.12 \times 10^{-7}$ | 1705 | 64 | 0.13 |
| 5 | $7.8 \times 10^{-7}$ | 1871 | 230 | 0.47 |
| 10 | $1.56 \times 10^{-6}$ | 2484 | 843 | 1.73 |
| 20 | $3.12 \times 10^{-6}$ | 2963 | 1322 | 2.71 |
| 50 | $7.8 \times 10^{-6}$ | 5123 | 3482 | 7.13 |
| 100 | $1.56 \times 10^{-5}$ | 8240 | 6599 | 13.51 |
| 200 | $3.12 \times 10^{-5}$ | 13,901 | 12,260 | 25.11 |
| 500 | $7.8 \times 10^{-5}$ | 27,400 | 25,759 | 52.75 |
| 1000 | $1.56 \times 10^{-4}$ | 37,532 | 35,891 | 73.50 |
| 2000 | $3.12 \times 10^{-4}$ | 46,501 | 44,860 | 91.87 |
| 5000 | $7.8 \times 10^{-4}$ | 50,159 | 48,518 | 99.36 |
| 10,000 | $1.56 \times 10^{-3}$ | 49,613 | 47,972 | 98.24 |
| 50,000 | $7.8 \times 10^{-3}$ | 50,739 | 40,098 | 100.54 |
| 100,000 | $1.56 \times 10^{-2}$ | 50,434 | 48,793 | 99.92 |

TABLE 3

Rate Constant of Probe in the Presence of Various Polymers and No Polymer Under Different Temperature and Salt Concentration Conditions

| Polymer | Temperature (° C.) | Salt Concentration (M) | Rate Constant ($M^{-1}s^{-1}$) |
|---|---|---|---|
| No Polymer | 60 | 0.45 | $5.7 \times 10^4$ |
| No Polymer | 40 | 0.15 | $1.45 \times 10^4$ |
| Poly-L-lysine hydrobromide (Low $M_w$ Poly-L-lysine) | 60 | 0.45 | $1 \times 10^5$ |
| Poly-L-lysine hydrobromide (High $M_w$ Poly-L-lysine) | 60 | 0.45 | $5.7 \times 10^4$ |
| Poly-L-lysine hydrobromide (High $M_w$ Poly-L-lysine) | 40 | 0.15 | $\geq 2 \times 10^7$ |
| Poly (lys, tyr) 4:1 | 60 | 0.45 | $6 \times 10^5$ |
| Poly-L-histidine hydrochloride | 60 | 0.45 | $5 \times 10^6$ |
| Poly-L-arginine hydrochloride | 60 | 0.45 | $5 \times 10^6$ |
| Poly-L-arginine hydrochloride | 40 | 0.15 | $\geq 2 \times 10^7$ |
| Hexadimethrine bromide | 60 | 0.15 | $3 \times 10^6$ |

The results of this experiment demonstrate that the presence of polycationic polymers in a reaction mixture can significantly enhance the rate of hybridization between a polynucleotide probe and a perfectly complementary target sequence. The results of this experiment further show that this enhanced rate of hybridization can be achieved using polycationic polymers under conditions promoting hybridization (e.g., high salt conditions).

Example 2

Effect of Polycationic Polymers on Hybridization Kinetics Between Probe and Mutant Target Sequences This example shows the effect that various polycationic polymers had on the rate at which a polynucleotide probe and a mutant target sequence associated under different combinations of salt and temperature conditions. The reagents, concentrations, times, conditions, tubes and instruments used in this example were identical to those of Example 1 above, except that a single base mismatch between the probe and the synthetic RNA target sequence was introduced at the fourth nucleotide position reading from the 5' end of the probe sequence. This was achieved by using the same target sequence as Example 1 and altering the probe to have the nucleotide base sequence of SEQ ID NO:3 gctgttgcgggactt(*)aacccaacat (the asterik indicates the location of a non-nucleotide linker). The rates listed below were determined in the same manner detailed above in Example 1.

TABLE 4

Rate Constant of Probe Containing a Single-Base Mismatch in the Presence of Various Polymers and No Polymer Under Identical Temperature and Salt Concentration Conditions

| Polymer | Temperature (° C.) | Salt Concentration (M) | Rate $(M^{-1}s^{-1})$ |
|---|---|---|---|
| No Polymer | 60 | 0.45 | $6 \times 10^3$ |
| Poly-L-lysine hydrobromide (Low $M_w$ Poly-L-lysine) | 60 | 0.45 | $1.5 \times 10^4$ |
| Poly (lys, tyr) 4:1 | 60 | 0.45 | $1 \times 10^5$ |
| Poly-L-histidine hydrochloride | 60 | 0.45 | $1.5 \times 10^6$ |
| Poly-L-arginine hydrochloride | 60 | 0.45 | $6 \times 10^6$ |
| Poly-L-arginine hydrochloride | 40 | 0.15 | $6 \times 10^6$ |
| Hexadimethrine bromide | 60 | 0.15 | $6 \times 10^6$ |

This experiment demonstrated that the presence of some polycationic polymers in a reaction mixture can enhance the rate of hybridization between a polynucleotide probe and a mutant target sequence having a single base mismatch to a sufficient degree to allow for the detection of different subtypes in a reaction mixture. Here, the results indicate that the poly-L-arginine hydrochloride (high salt concentration) and hexadimethrine bromide (low salt concentration) polymers tolerated the mismatch, whereas the remainder of the polymers tested were sensitive to the mismatch. The sensitivity of these remaining polymers suggests that they would enhance the rate of association between a probe and its complementary sequence while at the same time allowing for single base mismatch discrimination.

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

What I claim is:

1. In a homogenous assay method for detecting in a sample a hybrid formed between a labeled polynucleotide probe and a target polynucleotide in the presence of a polycationic polymer provided to the sample in an amount sufficient to increase the rate at which the hybrid is formed, the improvement comprising providing to the sample a dissociating reagent in an amount sufficient to dissociate the polycationic polymer from the hybrid after the polynucleotide probe and the target polynucleotide have had sufficient time to associate in the sample, and detecting the hybrid in the presence of unhybridized probe after the dissociating reagent has been provided to the sample.

2. The method of claim 1, wherein the probe polynucleotide and the polycationic polymer are in solution during the formation of the hybrid.

3. The method of claim 1, wherein the polycationic polymer is provided to the sample before the probe polynucleotide.

4. The method of claim 1, wherein the probe polynucleotide and the polycationic polymer are independently provided to the sample.

5. The method of claim 1, wherein the polycationic polymer is a homopolymer.

6. The method of claim 1, wherein the dissociating reagent is at least one of a polyanion and an anionic detergent.

7. The method of claim 6, wherein the dissociating reagent is an anionic detergent.

8. The method of claim 7, wherein the anionic detergent is lithium lauryl sulfate.

9. The method of claim 1, wherein the hybrid is in solution during the detecting step.

* * * * *

SEQUENCE LISTING

```
<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1
gctcgttgcg ggacttaacc caacat                                  26

<210> SEQ ID NO 2
<211> LENGTH: 26
<212> TYPE: RNA
<213> ORGANISM: Artificial Sequence
<220> FEATURE:
<223> OTHER INFORMATION: Synthetic Construct

<400> SEQUENCE: 2
auguuggguu aagucccgca acgagc                                  26

<210> SEQ ID NO 3
<211> LENGTH: 25
<212> TYPE: DNA
<213> ORGANISM: Artificial Sequence
<220> FEATURE:
<223> OTHER INFORMATION: Synthetic Construct

<400> SEQUENCE: 3
gctgttgcgg gacttaaccc aacat                                   25
```